US009918968B2

(12) United States Patent
Gaczynska et al.

(10) Patent No.: US 9,918,968 B2
(45) Date of Patent: Mar. 20, 2018

(54) RAPAMYCIN ANALOGS TARGETING PROTEASOME FUNCTION IN THE TREATMENT OF CANCER

(71) Applicant: THE BOARD OF REGENTS OF THE UNIVERSITY OF TEXAS SYSTEM, Austin, TX (US)

(72) Inventors: Maria E. Gaczynska, San Antonio, TX (US); Pawel A. Osmulski, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/652,825

(22) PCT Filed: Dec. 24, 2013

(86) PCT No.: PCT/US2013/077651
§ 371 (c)(1),
(2) Date: Jun. 17, 2015

(87) PCT Pub. No.: WO2014/107384
PCT Pub. Date: Jul. 10, 2014

(65) Prior Publication Data
US 2015/0328192 A1 Nov. 19, 2015

Related U.S. Application Data

(60) Provisional application No. 61/748,661, filed on Jan. 3, 2013.

(51) Int. Cl.
| | | |
|---|---|---|
| A61K 31/436 | (2006.01) | |
| A61K 45/06 | (2006.01) | |
| A61K 31/453 | (2006.01) | |
| A61K 31/69 | (2006.01) | |

(52) U.S. Cl.
CPC .......... *A61K 31/436* (2013.01); *A61K 31/453* (2013.01); *A61K 31/69* (2013.01); *A61K 45/06* (2013.01)

(58) Field of Classification Search
None
See application file for complete search history.

(56) References Cited

U.S. PATENT DOCUMENTS 5,252,579 A * 10/1993 Skotnicki ............. C07D 498/18
514/291
2010/0183728 A1* 7/2010 Desai ................... A61K 9/0019
424/489

FOREIGN PATENT DOCUMENTS

WO WO 2010/056733 5/2010

OTHER PUBLICATIONS

Mujtaba et al. Disc. Med., 2011, vol. 12, No. 67, pp. 471-480.*
Banaszynski et al., "Characterization of the FKBP-rapamycin-FRB ternary complex," *J. Am. Chem. Soc.*, 127: 4715-21, 2005.
Baselga et al., "Phase II Randomized Study of Neoadjuvant Everolimus Plus Letrozole Compared With Placebo Plus Letrozole in Patients With Estrogen Receptor-Positive Breast Cancer," *J. Clin. Oncology*, 27:2630-2637, 2009.
Bernstein-Molho et al., "Clinical activity of mTOR inhibition in combination with cyclophosphamide in the treatment of recurrent unresectable chondrosarcomas," *Cancer Chemother. Pharmacol.*, 70:855-60, 2012.
Cai et al., "In vitro metabolic study of temsirolimus: preparation, isolation, and identification of the metabolites," *Drug Metabol. Dispos.*, 35:1554-1563, 2007.
Chauhan et al., "Targeting proteasomes as therapy in multiple myeloma," *Advances in Experimental Medicine and Biology*, 615:251-260, 2008.
Crawford and Irvine, "Targeting the ubiquitin proteasome system in haematological malignancies," *Blood Reviews*, 27(6):297-304, 2013.
Cresta et al, "Phase I study of bortezomib with weekly paclitaxel in patients with advanced solid tumours," *European Journal of Cancer*, 44(13):1829-1834, 2008.
Dowling et al., "Current status and challenges associated with targeting mTOR for cancer therapy," *BioDrugs*, 23:77-91, 2009.
Engel et al., "A phase II study of single agent bortezomib in patients with metastatic breast cancer: a single institution experience," *Cancer Invest.*, 25(8):733-737, 2007.
Everly et al., "Bortezomib provides effective therapy for antibody- and cell-mediated acute rejection," *Transplantation*, 86(12):1754-61, 2008.
Extended European Search Report issued in European Patent Application No. 13869967.3, dated Jul. 20, 2016.
Farag et al., "Phase II trial of temsirolimus in patients with relapsed or refractory multiple myeloma," *Leukemia Research*, 43:1475-1482, 2009.
Gaczynska and Osmulski, "Harnessing proteasome dynamics and allostery in drug design," *Anitoxidants & Redox Signaling*, 21(17):2286-2301, 2014.
Gaczynska and Osmulski, "Small-molecule inhibitors of proteasome activity," *Methods in Molecular Biology*, 301:3-22, 2005.
Gaczynska and Osmulski, "Targeting protein-protein interactions in the proteasome super-assemblies," *Current Topics in Medicine Chemistry*, 15:2056-67, 2015.
Gaczynska et al., "Characterization of noncompetitive regulators of proteasome activity," In: Ubiquitin and Protein Degradation, Part A., *Methods in Enzymology.*, R.J. Deshaies, Ed., Elsevier, pp. 425-438, 2005.
Ghobrial et al., "Weekly bortezomib in combination with temsirolimus in relapsed or relapsed and refractory multiple myeloma: a multicentre, phase 1/2, open-label, dose-escalation study," *Lancet Oncol.*, 12:263-72, 2011.
Goodey and Benkovic, "Allosteric regulation and catalysis emerge via a common route," *Nature Chemical Biology*, 4:474-482, 2008.
Harrison et al., "Rapamycin fed late in life extends lifespan in genetically heterogeneous mice," *Nature*, 460:392-395, 2009.

(Continued)

Primary Examiner — Samira Jean-Louis
(74) Attorney, Agent, or Firm — Parker Highlander PLLC

(57) ABSTRACT

The invention provides for treatment of cancers using a rapamycin analog, optionally including bortezomib. In particular, the invention addresses the treatment of bortezomib-resistant cancers using seco-rapamycin and optionally a second proteasome inhibitor. This invention relates to oncology and medicine, and more particularly to treatment of cancer. In particular, rapamycin analogs such as seco-rapamycin may be used advantageously to target the proteasome in cancer cells, optionally in conjunction with proteasome inhibitors such as bortezomib.

31 Claims, 8 Drawing Sheets

(56) References Cited

OTHER PUBLICATIONS

Jankowska et al., "Potential allosteric modulators of the proteasome activity," *Biopolymers*, 93:481-495, 2010.

Jankowska et al., "The proteasome in health and disease," *Curr. Pharm. Design*, 19:1010-1028, 2013.

Kastritis et al., "Targeted therapies in multiple myeloma," *Targeted Oncology*, 4:23-36, 2009.

Liang et al., "Refined structure of the FKBP12-rapamycin-FRB ternary complex at 2.2 Å resolution," *Acta Crystallogr. Sect. D Biol. Cryst.*, 55:736, 1999.

Meyer et al., "Cyclosporine a is an uncompetitive inhibitor of proteasome activity and prevents NF-kB activation," *FEBS Letters*, 413:354-358, 1997.

Orlowski and Kuhn, "Proteasome inhibitors in cancer therapy: Lessons from the first decade," *Clinical Cancer Research*, 14:1649-1657, 2008.

Osmulski et al., "Rapamycin allosterically inhibits the proteasome," *Molecular Pharmacology*, 84(1):104-113, 2013.

PCT International Search Report and Written Opinion issued in International Patent Application No. PCT/US2013/077651, dated Mar. 21, 2014.

Suzuki et al., "Molecular mechanisms of bortezomib resistant adenocarcinoma cells," *PLoS One*, 6(12): e27996, 10 pages, 2011.

Wang et al., "Novel synergistic antitumor effects of rapamycin with bortezomib on hepatocellular carcinoma cells and orthotopic tumor model," *BMC Cancer*, 12:166, 2012.

Cai et al., "Topical calcineurin inhibitors in eczema and cancer association: A cohort study," *J. Dermatolog. Treat.*, 27(6):531-537, 2016. (Abstract).

Chang and Pearce, "Emerging concepts of T cell metabolism as a target of immunotherapy," *Nature Immunology*, 17(4):364-368, 2016.

Chaoul et al., "Rapamycin impairs antitumor $CD8^+$ T-cell responses and vaccine-induced tumor eradication," *Cancer Res.*, 75(16): 3279-91, 2015.

Deleuran et al., "Topical Calcineurin Inhibitors, Topical Glucocorticoids and Cancer in Children: A Nationwide Study," *Acta Derm. Venereol.*, 96(6):834-835, 2016.

Lane and Breuleux, "Optimal targeting of the mTORC1 kinase in human cancer," *Current Opinion in Cell Biology*, 21(2):219-229, 2009.

Lichtenberg et al., "The incidence of post-transplant cancer among kidney transplant recipients is associated with the level of tacrolimus exposure during the first year after transplantation," *Eur. J. Clin. Pharmacol.*, 73(7):819-826, 2017.

Ormerod, "Topical tacrolimus and pimecrolimus and the risk of cancer: how much cause for concern?" *Br. J. Dermatol.*, 153(4):701-705, 2005.

Sanchez-Perez, "Topical pimecrolimus and tacrolimus and the risk of cancer," *Actas Dermosifiliogr.*, 98(5):312-7, 2007.

\* cited by examiner

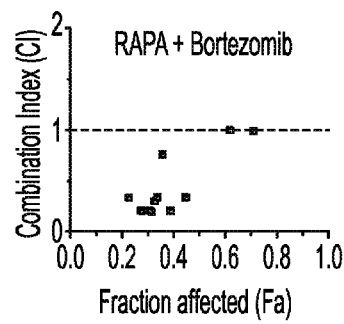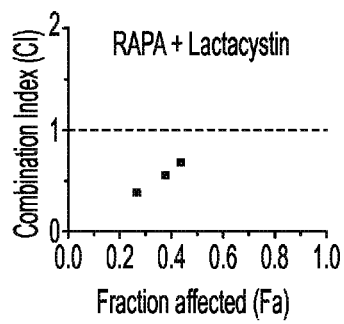
FIG. 10A   FIG. 10B
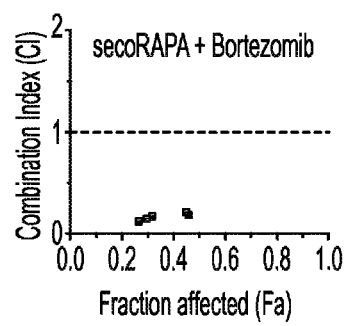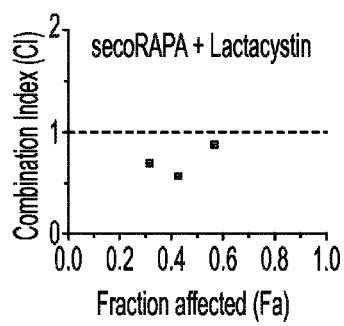
FIG. 10C   FIG. 10D
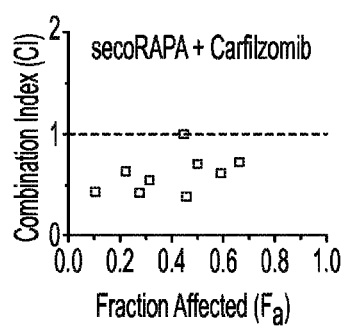
FIG. 10E though indicating some preferred embodiments of the invention, are given by way of illustration only, since various changes and modifications within the spirit and scope of the invention will become apparent to those skilled in the art from this detailed description.

RAPAMYCIN ANALOGS TARGETING PROTEASOME FUNCTION IN THE TREATMENT OF CANCER

This application is a national phase application under 35 U.S.C. § 371 of International Application No. PCT/US2013/077651, filed Dec. 24, 2013, which claims benefit of priority to U.S. Provisional Application Ser. No. 61/748,661, filed Jan. 3, 2013. The entire contents of the above-referenced disclosures are specifically incorporated herein by reference.

BACKGROUND OF THE INVENTION

1. Field of the Invention

This invention relates to oncology and medicine, and more particularly to treatment of cancer. In particular, rapamycin analogs such as seco-rapamycin may be used advantageously to target the proteasome in cancer cells, optionally in conjunction with proteasome inhibitors such as bortezomib.

2. Related Art

The phenomenon of allostery, broadly defined as coupling of conformational changes between distant sites, is one of fundamental regulatory mechanisms of enzymatic catalysis (Goodey and Benkovic, 2008). Therefore, it comes to no surprise that allosteric ligands are rapidly gaining recognition as attractive drug candidates. In fact, allosteric inhibitors exhibit many benefits over the commonly utilized competitive inhibitors. They provide a much broader range of mechanisms to interfere with catalysis. They are also more specific but less likely induce drug resistance.

One of the oldest examples of a successful allosteric drug is rapamycin (sirolimus). This natural macrocyclin binds the FKBP12 (FK-binding protein 12) with its FKBP binding domain, induces dimerization of FKBP12 and mTOR (mammalian target of rapamycin) and inhibits the latter with its effector domain binding to the allosteric side adjacent to the kinase domain (FIGS. 1A-D) (Liang et al., 1999 and Banaszynski et al., 2005). The mTOR kinase regulates translation, autophagy, response to hypoxia, and glucose metabolism (Dowling et al., 2009).

Rapamycin is an established immunosuppressive drug used to prevent transplant rejection. High doses of the drug are pro-apoptotic and close synthetic analogs of rapamycin (rapalogs) are used as effective anti-cancer agents (Dowling et al., 2009). In addition, animal studies revealed surprisingly strong anti-aging effects of a prolonged treatment with low doses of rapamycin (Harrison et al., 2009).

SUMMARY OF THE INVENTION

Thus, in accordance with the present invention, there is provided a method of inhibiting a cancer cell comprising contacting said cancer cell with seco-rapamycin in an amount sufficient to inhibit said cancer cell. The cancer cell may be bortezomib-resistant cancer cell. The method may further comprise contacting said cancer cell with a proteasome inhibitor binding to one or all types of proteasome active sites. The proteasome inhibitor may be selected from the group consisting of boronates (bortezomib, ixazomib, delanzomib), epoxyketones (carfilzomib, oprozomib), lactones (lactacystin/clasto-lactacystin beta-lactone, marizomib), aldehydes, vinyl sulfones and syrbactins. Contacting may occur multiple times, optionally wherein between multiple contacting events said cell is not exposed to seco-rapamycin. The may be cancer cell may not be a bortezomib-resistant cancer cell. The cancer cell may be a lung cancer cell, an ovarian cancer cell, a brain cancer cell, a pancreatic cancer cell, a cervical cancer cell, a head & neck cancer cell, a testicular cancer cell, a colon cancer cell, a bladder cancer cell, a liver cancer cell, a melanoma cell, a stomach cancer cell, an intestinal cancer cell, a prostate cancer cell, a breast cancer cell (including triple-negative breast cancer), a lymphoma cell, a leukemia cell or a myeloma cell. Inhibiting may comprise slowing growth of said cancer cell, inducing growth arrest of said cancer cell, or inducing death of said cancer cell. The method may further comprise contacting said cell with seco-rapamycin, a proteasome inhibitor and rapamycin or a rapalog.

In another embodiment, there is provided a method of treating a subject having cancer comprising administering to said subject with seco-rapamycin in an amount sufficient to inhibit said cancer cell. The cancer cell may be bortezomib-resistant cancer cell. The method may further comprise contacting said cancer cell with a proteasome inhibitor binding to one or all types of proteasome active sites. The proteasome inhibitor may be selected from the group consisting of boronates (bortezomib, ixazomib, delanzomib), epoxyketones (carfilzomib, oprozomib), lactones (lactacystin/clasto-lactacystin beta-lactone, marizomib), aldehydes, vinyl sulfones and syrbactins. Contacting may occur multiple times, optionally wherein between multiple contacting events said cell is not exposed to seco-rapamycin. The may be cancer cell may not be a bortezomib-resistant cancer cell. The cancer cell may be a lung cancer cell, an ovarian cancer cell, a brain cancer cell, a pancreatic cancer cell, a cervical cancer cell, a head & neck cancer cell, a testicular cancer cell, a colon cancer cell, a bladder cancer cell, a liver cancer cell, a melanoma cell, a stomach cancer cell, an intestinal cancer cell, a prostate cancer cell, a breast cancer cell (including triple-negative breast cancer), a lymphoma cell, a leukemia cell or a myeloma cell. Inhibiting may comprise slowing growth of said cancer cell, inducing growth arrest of said cancer cell, or inducing death of said cancer cell.

Treating may comprise slowing growth of said cancer, inducing growth arrest of said cancer, inducing programmed death in cells of said cancer, rendering an unresectable cancer resectable, inducing tumor tissue necrosis, extending said subject's lifespan, or improving said subject's quality of life. The subject may or may not have previously received bortezomib. The cancer may be recurrent and/or metastatic. Bortezomib may be administered prior to seco-rapamycin, after seco-rapamycin, at the same time a seco-rapamycin, or alternating with seco-rapamycin. Administering may comprise intravenous, intra-arterial, intra-tumoral, subcutaneous, topical or intraperitoneal administration, or may comprise local, regional, systemic, or continual administration. The subject may be a human. The method may further comprising administering to said subject seco-rapamycin, a proteasome inhibitor and rapamycin or a rapalog.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become more apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

(FIG. 1A) The canonical structure of rapamycin (sirolimus) with binding and effector domains marked. $R_1$ (red) designates the functional group attached to carbon-40 and distinguishing rapamycin from its synthetic analogs (rapalogs; below). (FIG. 1B) Single-domain rapamycin mimics $R_1$ (red) and $R_2$ (blue) designate functional groups of FK-506 and pimecrolimus (below). (FIG. 1C) Seco-rapamycin, the first physiological metabolite of rapamycin. The red dashed line marks breaking of the lactone ring. (FIG. 1D) Inhibitors of mTOR kinase structurally and mechanistically unrelated to rapamycin: PI-103 (left) and NVP-BEZ235 (right).

(FIG. 2A) the catalytic core proteasome, side and top views, based on 1ryp crystal structure (Groll et al., 1997). The gate area and groves on α face are marked. The groves are utilized for binding regulatory assemblies: PA200, 11S and 19S. (FIG. 2B) The assembly of PA200-20S-PA200, based on crystal structure 3L5Q; below: the amino acid sequence of human tPA200 peptide with HbYX motif underlined (Ortega et al., 2005). (FIG. 2C) The "activated proteasome" 11S-20S-11S, based on crystal structure 1fnt (Whitby et al., 2000), of 20S core in complex with PA26, a homolog of PA28/REG. (FIG. 2D) 26S assembly (19S-20S-19S), based on EM and molecular modeling (Lander et al., 2012), and the 1ryp crystal structure; below: the amino acid sequence of human tRpt5 peptide with HbYX motif underlined.

(FIG. 5A) AFM images of 20S proteasomes reveal the presence of two conformations: with smooth, convex α face ("closed") or with a dip (a darker spot) in the central area of α face ("open"). The leftmost panel presents a fragment of a field with imaged control proteasomes. Enlarged images of two top-view particles from the panel are presented on the right. Below the zoomed-in images are corresponding sections through the topmost 1 nm part of the α ring, as marked on the contour of the core proteasome on the bottom-right. The diagrams between the field fragment and the single molecule images demonstrate how the central sections in four directions (a-d) were run through the images to distinguish between closed and open conformers. In short, a particle is classified as closed if all four sections are convex, as in the case of particle "1". If all four sections are concave instead of convex, a particle is classified as open, as in the case of particle "2". The grey scale bar on the far right represents the height of the particles, from the baseline (black) to the top (white). The same height scale applies to single molecule images in FIG. 5B. (FIG. 5B) A gallery of zoomed-in images of control, DMSO-treated human proteasomes (top) and proteasomes treated with 0.2 µM-5 µM of rapamycin (bottom). The last three control images and the last six images of rapamycin-treated proteasomes represent particles in open conformation. (FIG. 5C) Treatment with rapamycin (rapa) promotes changes in conformational dynamics of proteasome particles. Single particle analysis was applied to images of proteasomes in continuously scanned fields, with a single scan lasting for nearly 3 minutes. Open and closed conformers are represented by open and black-filled circles, respectively. Each row in the diagrams represents a single proteasome particle imaged in consecutive scans of the same area. Each column represents particles from a single field. The top diagram represents four particles treated with 10 µM rapamycin. The bottom diagram represents four particles treated with 10 µM rapamycin, and then with the model substrate for the ChT-L peptidase (SucLLVY-MCA; 100 µM). All the particles retain the ability to switch between open and closed conformations. (FIG. 5D) Treatment of proteasomes with increasing concentrations of rapamycin results in decreasing ChT-L peptidase activity and decreasing content of closed conformers. Mean values±SD are presented for n=3 experiments (activity) or n=10-14 fields with 100-300 proteasome particles (partition of conformers). Differences in the % of closed conformers between control and each of the rapamycin-treated samples are statistically significant (p<0.001). (FIG. 5E) Proteasomes treated with a saturating concentration (10 µM) of distinct rapamycin-related compounds display undistinguishable partition of conformers and are refractory to conformational shift induced by a peptide substrate (SucLLVY-MCA; 100 µM). The partition of conformers in proteasomes incubated with PI-103 (10 µM) and then with the substrate was not significantly different from control and amounted for 74%±4% of closed particles (PI-103) vs. 29%±5% (PI-103, SucLLVY-MCA). Means values±SD; n=8-22 fields with 100-500 particles. The differences between the partition for control proteasomes+substrate and proteasomes pretreated with rapamycin related compounds before adding substrate are statistically significant (p<0.001). Rapa=rapamycin, pimecro=pimecrolimus. (FIG. 5F) Peptidase activities of proteasomes display varied sensitivity to treatment with a saturating concentration (10 µM) of distinct rapamycin-related compounds. The columns are grouped to point out the differences: the two-domain rapamycin stands out as the best inhibitor of the post-hydrophobic (ChT-L) peptidase, whereas both two-domain and one-domain derivatives strongly inhibit the post-acidic (PGPH) cleavages. Means values±SD; n=2 or 3 experiments.

(FIG. 8A) HeLa.S3 cervical carcinoma cells were refractory to the 48 hrs treatment with high nanomolar concentrations of bortezomib (BZ) or seco-rapamycin (sR) alone. However, the proliferation was impeded when the two inhibitors were combined. The number of live cells in control was counted as 100%. The number of dead cells in all cases varied from 3% to 14%, with 100% designating total (live+dead) cell count in control. (FIG. 8B) The proliferation of MCF7 breast carcinoma cells was not impeded by the 48 hrs treatment with bortezomib (BZ) or seco-rapamycin (sR) alone. However, the number of live cells dropped to less than half of the control number (100%) when the two drugs were combined. The dead cells count remained on the level of 6% to 16% (100%: total cell count in control), with the exception of about 60% in the samples treated with seco-rapamycin alone. (FIG. 8C) Seco-rapamycin attenuated growth of MDA-MB-231 (triple-negative breast cancer) cells. (FIG. 8D) Seco-rapamycin strongly synergized with bortezomib when MDA-MB-231 (triple-negative breast cancer) cells were treated with the drugs for 24 hours. Combination Index (CI) was calculated with the Chou-Talalay formalism. The effect is considered strongly synergistic for CI<0.3. The drugs alone affected viability of the cells only at high concentrations: EC50 (concentration required to exclude 50% of cells) for bortezomib was 745 nM, and for seco-rapamycin 869 nM.

Figures 1A, 1B, 1C, 1D:
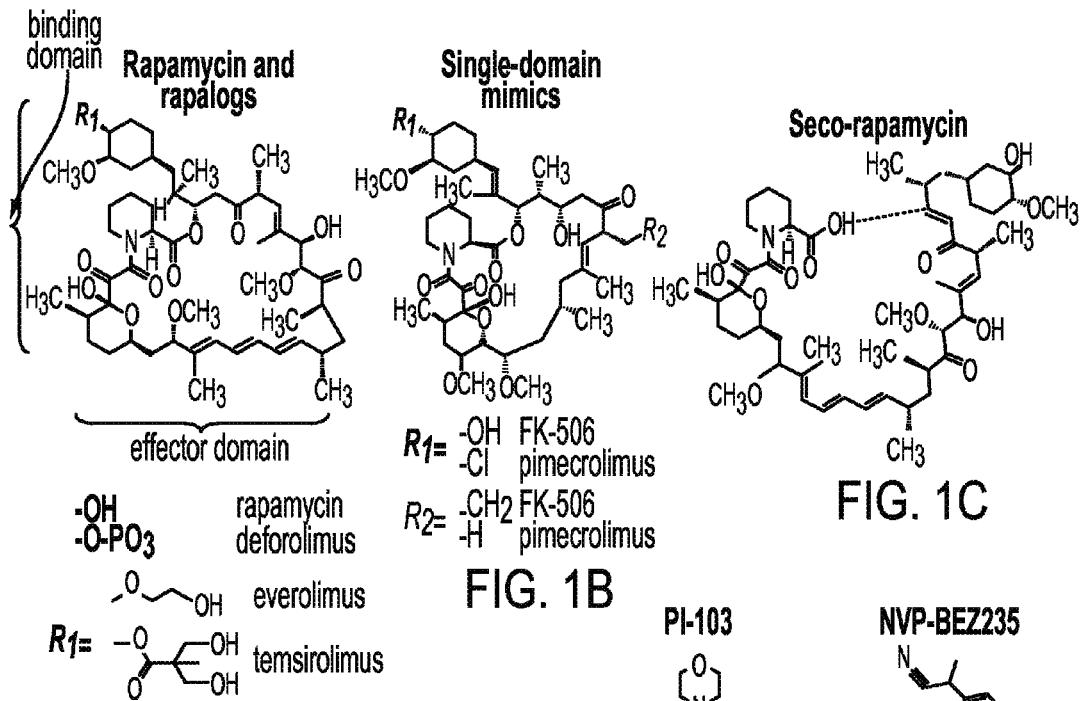
FIGS. 1A-D: The rapamycin and its derivatives used in the study.

Similarly, a combination of 5 nM BZ and 2 µM rapamycin left the ChT-L activity at the level of 53%, as compared 83% (BZ) and 70% (rapamycin) of activity remaining after the single drug treatment.

FIGS. 10A-E: Rapamycin and seco-rapamycin synergize in vitro with competitive inhibitors of the proteasome. The effects of combined treatments on the inhibition of ChT-L activity of human purified CP are presented. $IC_{50}$ for bortezomib was 77 nM, for carfilzomib 4 nM and for lactacystin 258 nM. Combination Index (CI) was calculated with the Chou-Talalay formalism. The effect is considered synergistic for CI<1, and strongly synergistic for CI<0.3. (FIG. 10A) rapamycin and bortezomib; (FIG. 10B) rapamycin and lactacystin; (FIG. 10C) seco-rapamycin and bortezomib; (FIG. 10D) seco-rapamycin and lactacystin; (FIG. 10E) seco-rapamycin and carfilzomib.

DESCRIPTION OF ILLUSTRATIVE EMBODIMENTS

The essential human enzyme called proteasome guards cellular homeostasis by degrading the bulk of intracellular proteins Inhibition of the proteasome is used in clinics to eliminate cancer cells. Other potential uses of regulation of enzymatic activity of the proteasome include attenuation of effects of inflammation in ischemic conditions and in auto-immune diseases, boosting immune response, and reducing deleterious effects of protein aggregation diseases. Such uses have been postulated, but not yet implemented in laboratory or clinical trials, due to a lack of suitable compounds.

The ability of rapamycin to modulate protein-protein interactions (discussed above) inspired the inventors to test if the drug would affect the activity of the multi-protein enzyme such as the proteasome. The proteasome constitutes the essential protease of the ubiquitin proteasome pathway. Majority of soluble intracellular proteins are processed by the pathway, which plays regulatory and housekeeping functions in every eukaryotic cell (Ciechanover, 2012). Similarly to mTOR, inhibition of proteasome leads to apoptosis, a feature already successfully used in cancer treatment (Dowling et al., 2009). A competitive proteasome inhibitor bortezomib (Velcade) is an approved anti-cancer drug and several other competitive inhibitors are undergoing clinical trials (Adams, 2004; Jankowska et al., 2013). Apart from cancer, proteasome is considered as attractive target for anti-inflammatory drugs (Tan et al., 2006).

The structural and functional complexity of the proteasome makes it to stand out among druggable enzymes. The proteasome is a multisubunit, multifunctional and modular protease (Groll et al., 1997). Three pairs of its active sites are concealed in the catalytic chamber inside the tube-shaped catalytic core built from four stacked rings (core particle; CP, 20S; FIGS. 2A-D). The sites exhibit chymotrypsin-like (ChT-L), trypsin-like (T-L) and post-acidic (PGPH; post-glutamyl peptide hydrolyzing) specificities cleaving polypeptides after hydrophobic, basic and acidic amino acid residues, respectively. Substrates reach the chamber through a gate formed by the noncatalytic α subunits. The activity of the CP is controlled by attachment of additional protein modules to the external surface on both sides of the 20S. The surface, called α face, harbors the gate and accepts the modules such as the 19S regulatory particle (RP), 11S (PA28/REG; proteasome activator/regulator) or PA200 activators (FIGS. 2A-D). A complex of the core with one or two (26S proteasome) multisubunit 19S "caps" recognizes and processes substrates tagged for degradation by polyubiquitinylation (Lander et al., 2012; Da Fonseca et al., 2012).

Polyubiquitinylated proteins comprise the majority of proteasomal substrates in vivo. The modules anchor in groves between α subunits, however the effects and mechanisms of binding are module-specific. For example, the attachment of RP to the α face is mediated by C-termini of selected Rpt (Rpt=regulatory particle ATPases) subunits, equipped with the Hb-Y-X motif (hydrophobic amino acid-Tyr-any amino acid) (Rabl et al., 2008). Hb-Y-X motif is also utilized by another module, a single-protein proteasome activator PA200 (Ortega et al., 2005). To the contrary, a heptameric proteasome activator/regulator PA28/REG anchors in the groves with C-termini devoid of Hb-Y-X, however the interaction is stabilized by activation loops interacting with the α face (Whitby et al., 2000).

The activity of the proteasome is allosterically regulated. The gate regulating substrate uptake can be opened by at least two distinct sets of allosteric signals: from catalytic chamber during certain stages of the enzymatic cycle, and from the groves on α face after binding the regulatory modules (Rabl et al., 2008, Whitby et al., 2000; Osmulski et al., 2009). The effects exerted by the modules on the catalytic performance of the core range from activation by the increased influx of substrates through the open gate, to shifts in peptidase specificities (Bajorek et al., 2003). The allosteric path between active sites and the α face is apparently utilized also for modulation of stability of the 26S assembly: binding the competitive inhibitor bortezomib stabilizes the 19S-20S (RP-CP) complex (Kleijnen et al., 2007). Moreover, an interesting hypothesis links activity in the catalytic chamber with cycles of changes in binding affinity between RP and CP (Babbitt et al., 2005).

Here, the inventors report that rapamycin, rapalogs and a rapamycin metabolite are allosteric inhibitors of the core proteasome. They interfere with substrate gating and with interactions between the 20S core and 19S components. The discovery suggests an intriguing possibility of rapamycin and its derivatives directly affecting both mTOR and ubiquitin-proteasome pathways in vivo. Even more important, it opens opportunity of designing a new class of allosteric proteasome inhibitors with potential anticancer properties, including those that do not exhibit the potentially problematic mTOR inhibition of Rapamycin.

I. Rapamycin And Rapalogs

Sirolimus, also known as rapamycin, is an immunosuppressant drug used to prevent rejection in organ transplantation; it is especially useful in kidney transplants. It prevents activation of T-cells and B-cells by inhibiting their response to interleukin-2 (IL-2). A macrolide, sirolimus was discovered by Brazilian researchers as a product of the bacterium *Streptomyces hygroscopicus* in a soil sample from Easter Island. It was approved by the FDA in September 1999 and is marketed under the trade name Rapamune by Pfizer.

Sirolimus was originally developed as an antifungal agent. However, this use was abandoned when it was discovered to have potent immunosuppressive and antiproliferative properties. It has since been shown to prolong the life of mice and might also be useful in the treatment of certain cancers. Sirolimus inhibits the response to interleukin-2 (IL-2), and thereby blocks activation of T- and B-cells. In contrast, tacrolimus inhibits the secretion of IL-2. The mode of action of sirolimus is to bind the cytosolic protein FK-binding protein 12 (FKBP12) in a manner similar to tacrolimus. Unlike the tacrolimus-FKBP12 complex, which inhibits calcineurin (PP2B), the sirolimus-FKBP12 complex inhibits the mammalian target of rapamycin (mTOR) pathway by directly binding the mTOR Complex1 (mTORC1). The rapamycin molecule is equipped with two distinct pharmacophores responsible for dimerization of mTOR with FKBP12 and allosteric inhibition of mTOR (Banaszynski et al., 2005, Liang et al., 1999) (FIGS. 1A-D).

Rapamycin and rapalogs are now shown here to affect stability of the 26S complexes. They do not interfere with stability of PA28 decorated proteasomes. By the destabilization of 26S proteasomes the compounds may limit capability of the enzyme to cleave polyubiquitinylated substrates. At the same time the free 20S, and especially PA28 decorated ("activated") proteasome may still preserve capacity to process unfolded proteins and oxidatively damaged proteins. Many of these substrates do not require polyUb. Preservation of PA28-decorated proteasome at the expense of 26S proteasome may be beneficial in slowing down cellular aging processes, when the proteasome machinery is apparently unable to effectively process the increased load of damaged protein substrates. Similarly, it may be beneficial in selected protein aggregation diseases, for example neurodegenerative diseases such as Parkinson's and others.

The chief advantage sirolimus has over calcineurin inhibitors is its low toxicity towards kidneys. Transplant patients maintained on calcineurin inhibitors long-term tend to develop impaired kidney function or even chronic renal failure; this can be avoided by using sirolimus instead. It is particularly advantageous in patients with kidney transplants for hemolytic-uremic syndrome, as this disease is likely to recur in the transplanted kidney if a calcineurin-inhibitor is used. However, on Oct. 7, 2008, the FDA approved safety-labeling revisions for sirolimus to warn of the risk for decreased renal function associated with its use.

Sirolimus can also be used alone, or in conjunction with calcineurin inhibitors, such as tacrolimus and/or mycophenolate mofetil, to provide steroid-free immunosuppression regimens. Impaired wound healing and thrombocytopenia are possible side effects of sirolimus; therefore, some transplant centres prefer not to use it immediately after the transplant operation, but instead administer it only after a period of weeks or months. Its optimal role in immunosuppression has not yet been determined, and is the subject of a number of ongoing clinical trials.

Sirolimus is absorbed into the blood stream from the intestine variably in each patient, with some patients having up to eight times more exposure than others for the same dose. Drug levels are therefore taken to make sure patients get the right dose for their condition. This is determined by taking a blood sample before the next dose, which gives the trough level. Fortunately, there is good correlation between trough concentration levels and drug exposure, known as area under the concentration-time curve, for both sirolimus (SRL) and tacrolimus (TAC) (SRL: r2=0.83; TAC: r2=0.82), so only one level need be taken to know its pharmacokinetic (PK) profile. PK profiles of SRL and of TAC are unaltered by simultaneous administration. Dose-corrected drug exposure of TAC correlates with SRL (r2=0.8), so patients have similar bioavailability of both.

The antiproliferative effect of sirolimus has also been used in conjunction with coronary stents to prevent restenosis in coronary arteries following balloon angioplasty. The sirolimus is formulated in a polymer coating that affords controlled release through the healing period following coronary intervention. Several large clinical studies have demonstrated lower restenosis rates in patients treated with sirolimus-eluting stents when compared to bare metal stents, resulting in fewer repeat procedures. A sirolimus-eluting coronary stent is marketed by Cordis under the tradename Cypher. It has been proposed, however, that such stents may increase the risk of vascular thrombosis.

Lung toxicity is a serious complication associated with sirolimus therapy, especially in the case of lung transplants. The mechanism of the interstitial pneumonitis caused by sirolimus and other macrolide mTOR inhibitors is unclear, and may have nothing to do with the mTOR pathway. The interstitial pneumonitis is not dose dependent, but is more common in patients with underlying lung disease.

As with all immunosuppressive medications, rapamycin may decrease the body's inherent anticancer activity and allow some cancers, which would have been naturally destroyed to proliferate. Patients on immunosuppressive medications have a 10- to 100-fold increased risk of cancer compared to the general population. Historically, approximately 10% of solid organ recipients treated with calcineurin inhibitors develop skin tumors and lymphoma after 70 months. However, there is contradictory data regarding calcineurin inhibitors versus rapamycin via UV-induced carcinogenesis-associated processes such as DNA repair, p53 and MMP expression as a result from different biochemical mechanisms. People who currently have or have already been treated for cancer have a higher rate of tumor progression and recurrence than patients with an intact immune system. These general considerations counsel caution when exploring the potential of rapamycin to combat cancer, which is suggested by experiment. Rapamycin seems to lower the cancer risk in some transplant patients.

Rapamycin inhibits a protein kinase complex known as mTORC1, and this appears to provide most of the beneficial effects of the drug (including life-lengthening in animal studies). Rapamycin also acts on a related complex known as mTORC2. Disruption of mTORC2 produces the diabetes-like symptoms of decreased glucose tolerance and insensitivity to insulin also associated with rapamycin.

II. The Proteasome

The proteasome is a multisubunit protease (Groll et al., 1997). Its active sites are concealed inside the tube-shaped catalytic core (CP, 20S; FIGS. 2A-D) and, in the human, exhibit chymotrypsin-like (ChT-L), trypsin-like (T-L) and post-acidic (PGPH; post-glutamyl peptide hydrolyzing) specificities. Substrates reach the centers through an allosterically regulated gate. Even subtle shifts in proteasome specificity are clinically relevant. For example, two competitive inhibitors bortezomib and marizomib (NPI-0052; salinosporamide A) are successfully used in combination treatments likely because of small but significant differences in their affinity to active sites (Fenical et al., 2009).

Because of modular architecture, several proteolytic assemblies are designated by the "proteasome" name, all of them sharing the 700 kilodaltons (kDa), 20S catalytic core particle. The size of the 20S core proteasome is relatively conserved and is about 150 angstroms (Å) by 115 Å. The interior chamber is at most 53 Å wide, though the entrance can be as narrow as 13 Å, suggesting that substrate proteins must be at least partially unfolded to enter. The "20S" relates to the Svedberg sedimentation coefficient (sedimentation rate; denoted "S"), and the proteasome subcomponents are often referred by their respective Svedberg units. The most common form of the higher order proteasome assembly is known as the 26S proteasome, which is about 2000 kDa in molecular mass and contains one 20S core particle structure and two 19S regulatory caps. The core is hollow and provides an enclosed cavity in which proteins are degraded; openings at the two ends of the core allow the target protein to enter. Each end of the core particle associates with a 19S regulatory subunit that contains multiple ATPase active sites and ubiquitin binding sites; it is this structure that recognizes polyubiquitinated proteins and transfers them to the catalytic core. Alternative forms of regulatory modules called the 11S particle (proteasome activator PA28/REG) and the PA200 activator can associate with the core through the same binding sites as the 19S particle, however with somehow distinct binding mechanism. The αβ form of the multisubunit 11S activator may play a role in degradation of foreign peptides such as those produced after infection by a virus.

The number and diversity of subassemblies and subunits contained in the assemblies under the "proteasome" name depends on the organism; the number of distinct and specialized subunits is larger in multicellular than unicellular organisms and larger in eukaryotes than in prokaryotes. All 20S particles consist of four stacked heptameric ring structures that are themselves composed of two different types of subunits; α subunits are structural in nature, whereas at least some of β subunits are catalytic. The outer two rings (α rings) in the stack consist of seven α subunits each, named α1 to α7 and numbered in a counter clockwise manner, when looking from the outside of the 20S proteasome. The α subunits serve as docking domains for the regulatory particles. N-termini of alpha subunits form a gate that blocks unregulated access of substrates to the interior cavity. The inner two rings each consist of seven β subunits and contain the protease active sites that perform the proteolysis reactions. In Archaea such as *Thermoplasma acidophilum*, all the α and all the β subunits are identical, and all β subunits harbor identical active sites. Eukaryotic proteasomes such as those in yeast contain seven distinct types of a and seven types of β subunits, designated α1-α7 and β1-β7, respectively. In Eukaryota there are three pairs of active centers capable to cleave a variety of polypeptides on the carboxyl site of hydrophobic (and branched), basic, and acidic (plus small and neutral) amino acids. The three kinds of endopeptidolytic activities are called chymotrypsin-like (ChT-L), trypsin-like (T-L) and post-acidic (caspase-like; post-glutamyl peptide hydrolyzing, PGPH), and are harbored by the β5, β2 and β1 subunits, respectively. All proteasomal active sites active sites regardless of specificity share a common mechanism of N-terminal nucleophile, and more specifically N-terminal threonine protease type. In addition to the "housekeeping" set of β1, β2 and β5 catalytic subunits, there is another exchangeable set: β5i-β2i-β1i ("i" stands for "immuno") forming immunoproteasomes and also a tissue-specific ensemble β5t-β2i-β1i ("t" stands for "thymus") confined to thymus. In many tissues the expression of immunosubunits is up-regulated by inflammatory signals such as cytokines, in particular, interferon gamma (γ-IFN), together with expression of many immune response related proteins, including subunits of the αβ form of the 11S activator. All three types of core proteasomes can perform all the basic protein degradation chores. However, subtle differences in the structure of active site pockets of the distinct variants of subunits account for physiologically meaningful shifts in specificities of cleavages. For example, the increase in ChT-L and T-L cleavages in immunoproteasomes is perfectly suited for enhanced production of antigenic peptides by the proteasomes, with the peptides originating in viral or mutated proteins and used by the immune system to detect virally infected cells or cells bearing harmful mutated proteins.

The 19S particle (regulatory particle; RP) in eukaryotes is built from thirteen Rpn (regulatory particle non-ATPases) and six Rpt (RP ATPases) subunits, can be dissected into the ten-subunit base and nine-subunit lid, the former responsible for ATP-dependent unfolding of polypeptides with a reverse-chaperone mechanism The ATPase subunits belong to the widespread AAA Family, and an evolutionary homolog of these ATPases exists in Archaea, called PAN (Proteasome-Activating Nucleotidase). Recent advances in cryo-electron microscopy and molecular modeling brought elegant models of the six ATPases of the base arranged as a spiral staircase on the α face, and the lid subunits attached to both the α ring and the base, with receptor subunits perfectly positioned to bind polyubiquitin chains or specific shuttle proteins carrying polyubiquitinated substrates. The association of the 19S and 20S particles requires the binding of ATP to the 19S ATPase subunits, and ATP hydrolysis is required for the assembled complex to degrade folded and ubiquitinated proteins. Note that only the step of substrate unfolding requires energy from ATP hydrolysis, while ATP-binding alone can support all the other steps required for protein degradation (e.g., complex assembly, gate opening, translocation, and proteolysis). In fact, ATP binding to the ATPases by itself supports the rapid degradation of unfolded proteins. However, while ATP hydrolysis is required for unfolding only, it is not yet clear whether this energy may be used in the coupling of some of these steps. Nevertheless, it is understood, in general, how the 19S associates with and regulates the 20S core particle (Smith et al., 2007). In fact, the 19S and 11S particles bind to the same sites in the α rings of the 20S core particle although, they each induce gate opening by different mechanism.

The mechanism by which the proteasomal ATPase open this gate has been recently elucidated. 20S gate opening, and thus substrate degradation, requires the C-termini of the proteasomal ATPases, which contains a specific motif (i.e., HbYX motif). The ATPases C-termini bind into pockets in the top of the 20S, and tether the ATPase complex to the 20S proteolytic complex, thus joining the substrate unfolding equipment with the 20S degradation machinery. Binding of these C-termini into these 20S pockets by themselves stimulates opening of the gate in the 20S subunit (Smith et al., 2007).

On the other hand, the 11S regulatory particle is a heptameric structure that does not contain any ATPases, does not bind polyubiquitin chains, and can promote the degradation of short peptides and unfolded proteins but fully folded proteins. It is presumed that 11S wide-opens the gate, however does not promote protein unfolding. This structure is also known as PA28 or REG. It binds to the core particle through the C-terminal tails of its subunits. The tails do not contain HbYX or similar motifs, however they are supported by activation loops protruding from 11S subunits and interacting with the α ring of the 20S core. 11S induces α-ring conformational changes to open the 20S gate in a mechanism believed to be generally similar to that of the 19S particle. There are two forms of the heptameric 11S complex, one containing PA28α and PA28β subunits, and another built from PA28γ subunits. The expression of the αβ form of the 11S particle is induced by interferon gamma and is responsible, in conjunction with the immunoproteasomes, for the generation of peptides that bind to the major histocompatibility class I complex. The γ form of 11S is believed to be involved in interactions of the proteasome with specific protein ligands, especially in the nucleus. Both forms promote opening of the proteasome gate, however they invoke distinct shifts in specificities of the core active centers (Rechsteiner and Hill, 2005).

Summarizing, the external surface on both sides of the 20S (α face; FIGS. 2A-D) accepts the regulatory modules such as the most physiologically relevant 19S regulatory particle (RP), 11S activator complex or PA200 single-protein activator. A core with one or two (26S complex) 19S "caps" recognizes and processes substrates tagged for degradation by polyubiquitination. De novo assembly of multisubunit 19S is assisted by chaperones (Funakoshi et al., 2009, Roelofs et al., 2009), however RP and CP may undergo multiple cycles of association—dissociation (Babbitt et al., 2005). Stability of 19S-20S complex, important for its performance, is controlled by ATP (Liu et al., 2006), BZ (stabilization (Kleijnen et al., 2007) and by allosteric ligands (Gaczynska et al., 2003). The activity and specificity of the CP and stability of assemblies are allosterically regulated (Rechsteiner and Hill, 2005; Kleijnen et al., 2007; Osmulski et al., 2009; Sprangers and Kay, 2007). Identifying rapamycin as a destabilizer of 26S and a non-competitive/allosteric inhibitor and specificity regulator of 20S proteasome opens new venues for drug design. So far, only limited data suggested changes in the UPP upon rapamycin treatment. The data included lowered expression of 11S proteasome activator subunits, accompanied by lowered proteasome activity in rapamycin-treated human peripheral blood mononuclear cells (Wang et al., 1997). An increased activity was observed in extracts of treated murine macrophages (Jin et al., 2009). No systematic studies on the performance of UPP in cells or organisms treated with rapamycin/rapalogs were conducted.

III. Proteasome Inhibitors

A. Bortezomib

Bortezomib is approved to treat malignancies with the upregulated NFκB such as multiple myeloma (MM) and lymphomas (Orlowski and Kuhn, 2008), alone or in combination therapies (Everly et al., 2008). Results of BZ trials with other than blood cancers are mixed (Cresta et al, 2008; Engel et al., 2007). Another inhibitor of the proteasome, carfilzomib (Kyprolis, PR-171) has been recently approved for treatment of blood malignancies, and four additional inhibitors of the proteasome, marizomib (salinosporamide A, NPI-0052), ixazomib (MLN9708), delanzomib (CEP-18770) and oprozomib (ONX 0912), currently undergo trials with blood cancers (Crawford and Irvine, 2013, Jankowska et al., 2013). The upregulation of NFκB does not guarantee strong response to BZ, as in the case of renal cell carcinomas (RCC) (Vaziri et al., 2010). The RCCs with their activated mTOR pathway and disregulated hypoxic response are rational targets for rapalogs, such as temsirolimus (Torisel) and everolimus (Afinitor); however, the mechanism of rapalog actions is unclear (Konings et al., 2009). Multiple trials showed some success of rapalogs with breast cancers (Baselga et al., 2009), and only a modest success with MM (Farag et al., 2009). Trials involving BZ or rapalogs with other drugs are abundant, however combining BZ and rapalogs is infrequent, with encouraging results for lymphoid cancers. In none of these trials the direct effects of rapalogs on the proteasome were suspected or anticipated.

B. Carfilzomib

Carfilzomib (Kyprolis™) is derived from epoxomicin, a natural product that was shown by the laboratory of Craig Crews at Yale University to inhibit the proteasome. The Crews laboratory subsequently invented a more specific derivative of epoxomicin named YU101, which was licensed to Proteolix, Inc. Scientists at Proteolix modified YU101 to create carfilzomib, which they advanced to multiple Phase 1 and 2 clinical trials, including a pivotal Phase 2 clinical trial designed to seek accelerated approval. Clinical trials for carfilzomib continue under Onyx Pharmaceuticals, which acquired Proteolix in 2009. In January 2011, the U.S. FDA granted carfilzomib fast-track status, allowing Onyx to initiate a rolling submission of its new drug application for carfilzomib. In December 2011, the FDA granted Onyx standard review designation, for its new drug application submission based on the 003-A1 study, an open-label, single-arm Phase 2b trial. The trial evaluated 266 heavily-pretreated patients with relapsed and refractory multiple myeloma who had received at least two prior therapies, including bortezomib and either thalidomide or lenalidomide. Carfilzomib was approved by the FDA for use in patients with relapsed and refractory multiple myeloma on 20 Jul. 2012. Carfilzomib based therapy costs $10,000 per 28-day cycle, making it the most expensive FDA-approved drug for multiple myeloma.

C. Oprozomib

Onyx is developing oprozomib (ONX 0912; N—((S)-3-methoxy-1-(((S)-3-methoxy-1-(((S)-1-((R)-2-methyloxiran-2-yl)-1-oxo-3-phenylpropan-2-yl)amino)-1-oxopropan-2-yl)amino)-1-oxopropan-2-yl)-2-methylthiazole-5-carboxamide), a novel oral proteasome inhibitor from the class of epoxyketones. In preclinical studies, oprozomib has been shown to inhibit the 20S proteasome that primarily targets chymotrypsin-like activity. Oprozomib is distinct from carfilzomib, although the compound is based on the same chemistry that is employed to selectively target the proteasome. As an orally-dosed agent, oprozomib is designed to provide prolonged proteasome inhibition and combinability with other available therapies with the convenience of an oral therapy.

Oprozomib has demonstrated preclinical anti-tumor activity and a broad therapeutic window in preclinical models. Oprozomib is currently being studied in two trials, including a Phase 1b/2 study evaluating oprozomib in hematologic malignancies including multiple myeloma. The second trial is a Phase 1 study in patients with recurrent or refractory solid tumors. From this early-stage study, data from this trial have shown that two-thirds of patients at the 90 mg dose or above achieved a level of proteasome inhibition comparable to what has been observed with carfilzomib, although further study is required.

D. Delanzomib

Delanzomib (CEP-18770) is a potent chymotrypsin-like proteasome inhibitor with an $IC_{50}$ of 3.8 nM. Delanzomib prevents the proliferation of several tumor cell lines, such as A2780 ovarian cancer cells, PC3 prostate cancer, H460, LoVo colon cancer, RPMI8226 multiple myeloma cancer and HS-Sultan anaplastic non-Hodgkin lymphoma with $IC_{50}$ of 13.7, 22.2, 34.2 11.3, 5.6 and 8.2 nM, respectively. The $IC_{50}$ values of Delanzomib are similar to those of bortezomib, with the chymotryptic and caspase-like activities being inhibited at low-nanomolar concentrations. Similarly to bortezomib, boronate is the active group in Delanzomib.

Delanzomib blocks the ubiquitin-proteasome pathway in several MM and in the chronic myelogenous leukemia cell line, K562. Delanzomib gives rise to an accumulation of polyubiquitinated proteins over 4 to 8 hours with a profile similar to that observed after bortezomib treatment. Delanzomib completely blocks the degradation of IκBa. Delanzomib markedly decreases high levels of NF-κB activity in both RPMI-8226 and U266 cells. The time- and concentration-dependent suppression of NF-κB DNA-binding activity in MM cell lines by Delanzomib leads to a decrease of several NF-κB-modulated genes mediating the growth and survival of tumor cells including IκBa itself, the X-chromosome-linked inhibitor-of-apoptosis protein (XIAP), the pro-inflammatory cytokines TNF-α and interleukin-1β (IL-1β), the intracellular adhesion molecule (ICAM1), and the pro-angiogeneic factor vascular endothelial growth factor. The proapoptotic activity of Delanzomib against MM is not limited solely to tumor-derived MM cell lines, but extends to primary MM explants from relapsed or refractory patients including those previously treated with bortezomib. In addition, the combination of Delanzomib with melphalan or bortezomib generates synergistic prevention of MM cell viability in vitro.

Delanzomib reveals sustained and dose-related relative tumor weight inhibition. Delanzomib leads to dose-related induction of complete tumor regressions, as compared with bortezomib treatment, which results in a 50% incidence of CR at its maximally tolerated dose (MTD) of 1.2 mg/kg intravenously. In contrast to bortezomib, Delanzomib reveals dose-related increases in the incidence of tumor-free mice by the completion of these studies (120 days after tumor transplantation). Oral administration of Delanzomib yields a marked decrease of tumor weight and notable dose-related incidence of complete tumor regression with minimal changes in animal body weight over the course of 120 day studies. Relative to bortezomib, equiactive doses of Delanzomib reveals a greater and more sustained dose-related inhibition of tumor proteasome activity, corresponding temporally with maximum induction of caspase-3 and 7 activity. The maximum apoptotic signal is 2.5-fold greater for Delanzomib versus bortezomib. In contrast, proteasome inhibition profiles of Delanzomib and bortezomib are comparable in the normal peripheral mouse tissues examined (liver, lungs, whole blood, and brain) in both their magnitude and their duration. No proteasome inhibition is detected in brain tissue at any time point for Delanzomib or bortezomib.

In MM xenograft models, the addition of Delanzomib to melphalan completely prevents the growth of both melphalan-sensitive and melphalan-resistant tumors. The combination of Delanzomib and bortezomib gives rise to complete regression of bortezomib-sensitive tumors and markedly delays progression of bortezomib-resistant tumors compared to treatment with either agent alone. Single agent Delanzomib PO also shows marked anti-MM effects in these xenograft models. Administration of single-agent Delanzomib yields a dose-dependent reduction in paraprotein secretion from LAGκ-1A tumors. Delanzomib delivered orally also inhibits tumor growth. After only 14 d of treatment with oral Delanzomib, a marked decrease in tumor volume is observed compared with control-treated tumors. Compared with control-treated mice, mice treated with Delanzomib twice weekly at 3 mg/kg i.v. or 10 mg/kg orally exhibits tumors are approximately 8 or 12 times smaller following 14 d of treatment.

E. Ixazomib

Ixazomib (MLN9708) is the first orally available proteasome inhibitor in clinical trials. It is now undergoing Phase 1 and 2 evaluations for lymphoma. Ixazomib is a boron-containing peptide, which in aqueous environment hydrolyses to biologically active boronate form (MLN2238). It dissociates from the proteasome easier than the practically irreversible bortezomib, and its tissue distribution differ substantially from that of bortezomib. Preclinical studies suggested that it might be effective with both blood and solid cancers, however the notion has not been verified in clinic.

F. Marizomib

Marizomib (NPI-0052, salinosporamide A; (1R,4R,5S)-4-(2-chloroethyl)-1-((S)-cyclohex-2-en-1-yl(hydroxy) methyl)-5-methyl-6-oxa-2-azabicyclo[3.2.0]heptane-3,7-dione) is a naturally-occurring salinosporamide, isolated from the marine actinomycete *Salinospora tropica*, with potential antineoplastic activity. Marizomib irreversibly binds to and inhibits the 20S catalytic core subunit of the proteasome by covalently modifying its active site threonine residues; inhibition of ubiquitin-proteasome mediated proteolysis results in an accumulation of poly-ubiquitinated proteins, which may result in the disruption of cellular processes, cell cycle arrest, the induction of apoptosis, and the inhibition of tumor growth and angiogenesis. This agent more may more potent and selective than the proteasome inhibitor bortezomib. Marizomib belongs to lactone-based proteasome inhibitors. The first proteasome inhibitor from this group, and the first specific non-peptidic proteasome inhibitor discovered was lactacystin.

Lactacystin is an organic compound naturally synthesized by bacteria of the genus *Streptomyces* first described in 1991. The molecule is a lactam, or cyclic amide. The first total synthesis of lactacystin was developed in 1992. Lactacystin is widely used as a research tool in biochemistry and cell biology. Lactacystin in aqueous environment rapidly forms clasto-lactacystin-beta lactone, which covalently modifies the amino-terminal threonine of specific catalytic subunits of the proteasome, a discovery that helped to establish the proteasome as a mechanistically novel class of protease: an amino-terminal threonine protease (Jankowska et al., 2013).

G. Vinyl Sulfones, Aldehydes and Syrbactins.

In addition to the peptide boronates, peptide epoxyketones and lactones, which have representative compounds already under clinical evaluation, there are other classes of competitive inhibitors characterized by a reasonable specificity and potency towards the proteasome but not yet developed into clinical use. All of these compounds block the active sites of the proteasome, as do the compounds described above. The inhibitors, which did not yet advanced to clinic, include peptide aldehydes and peptide vinyl sulfones, with aldehyde and vinyl sulfone active groups binding to the proteasome active sites. Some of these compounds are popular research tools, most notable aldehyde MG132 (Cbz-LLL-CHO) and trileucine vinyl sulfones blocked with aminohexanoic acid derivative or with carbobenzoxy group (Gaczynska and Osmulski, 2005). Natural products syrbactins such as syringolin A and glidobactin A constitute a separate class of competitive inhibitors covalently binding to the proteasome active centers and exhibiting anti-proliferating activities in cell culture studies (Groll et al., 2008; Coleman et al., 2006).

H. Allosteric Ligands

Contrary to competitive inhibitors, the small-molecule allosteric ligands of the proteasome are much less explored (Tan et al., 2006). They include Pro and Arg rich (PR) peptides, which bind to the α face, destabilize the gate and the RP-CP interactions, and affect peptidase activities in vitro (Gaczynska et al., 2003). In vivo, PR peptides inhibit degradation of selected substrates and display anti-inflammatory and pro-angiogenic properties (Gao et al., 2000). The α face is also a docking place for short peptide derived from protein ligands of CP: the HIV-Tat protein, Rpt subunits, PA28 or PA200. Such peptides are reportedly able to mimic some allosteric effects of their parent proteins (Jankowska et al., 2010). There is also an example of an allosteric inhibitor, 5-amino-8-hydroxyquinoline (5AHQ) binding inside the antechamber (Li et al., 2010, de Wilt et al., 2012).

IV. Therapies

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render materials stable and allow for uptake by target cells. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the analogs of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Cancer Types and Subjects

Cancer cells to which the methods of the present invention can be applied include generally any cancer cell. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

C. Treatment Methods

The agents of the present invention may be provided alone or in conjunction with other drugs and/or radiotherapy, in particular anti-proteasome therapies. The compounds can also be administered to subjects that are genetically and/or environmentally (due to, for example, physiological and/or environmental factors) susceptible to cancer, e.g., subjects with a family history of cancer, subjects with chronic inflammation or subject to chronic stress, or subjects that are exposed to natural or non-natural environmental carcinogenic conditions (e.g., excessive exposure to sunlight, industrial carcinogens, or tobacco smoke).

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 5-, 6-, 8-, 10-, 20-, 50-, 100-, 150-, or more times).

D. Combination Therapies

As mentioned above, it is not unusual for cancers to develop into drug-resistant cancers. One general approach to such problems combine cancer therapies as a way of increasing their efficacy. While such approaches can be successful, it is entirely unclear whether any two therapies will work in concert to inhibit a given type of cancer. In the context of the present invention, the inventors have shown that seco-rapamycin therapy can be used successfully in conjunction with another anti-proteasomal agent to render resistant cells sensitive to treatment.

To kill cells, inhibit cell growth, inhibit metastasis, inhibit angiogenesis or otherwise reverse or reduce the malignant phenotype of tumor cells, using the methods and compositions of the present invention, one would generally contact a target cell with a rapamycin analog, and another anti-proteasomal therapy. These therapies would be provided in a combined amount effective to kill or inhibit proliferation of the cell/cancer. This process may involve contacting the cells/patient with the agents/therapies at the same time. This may be achieved by contacting the cell with a single composition or pharmacological formulation that includes both therapies, or by contacting the cell with two distinct compositions or formulations, at the same time, wherein one composition includes the analog and the anti-proteasomal therapy.

Alternatively, the analog treatment may precede or follow the anti-proteasomal therapy by intervals ranging from minutes to weeks. In embodiments where the anti-proteasomal therapy and the analog are applied separately to the cell or subject, one would generally ensure that a significant period of time did not expire between the time of each delivery, such that the therapies would still be able to exert an advantageously combined effect on the cell/cancer. In such instances, it is contemplated that one would contact the cell/patient with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the analog or the anti-proteasomal therapy will be desired. Various combinations may be employed, where the analog is "A" and the anti-proteasomal therapy is "B," as exemplified below:

| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are contemplated. Again, to achieve cell killing, both therapies are delivered to a cell in a combined amount effective to kill the cell.

E. Additional Combinations

In conjunction with the aforementioned combination therapy, other agents or factors or therapies may be suitable for combined use. These include can include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition.

Various classes of chemotherapeutic agents are contemplated for use with in combination with analogs of the present invention, for example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use include, e.g., camptothecin, actinomycin-D and mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with an analog, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include Adriamycin, also known as Doxorubicin, Etoposide, Verapamil, Podophyllotoxin, and the like. Widely used in a clinical setting for the treatment of neoplasms, these compounds are administered through bolus injections intravenously at doses ranging from 25-75 mg/m$^2$ at 21 day intervals for Doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy with the analogs claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU is applicable in a wide range of carriers, including topical. Intravenous administration with doses ranging from 3 to 15 mg/kg/day is commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors affect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of analogs to patients with cancer will be a very efficient method for treating the clinical disease. Similarly, the chemo- or radiotherapy may be directed to a particular, affected region of the subject's body. Alternatively, regional or systemic delivery of expression construct and/or the agent may be appropriate in certain circumstances, for example, where extensive metastasis has occurred.

In addition to combining Rapamycin analog therapies with chemo- and radiotherapies, it also is contemplated that combination with immunotherapy, hormone therapy, toxin therapy and surgery.

It also should be pointed out that any of the foregoing therapies may prove useful by themselves in treating cancer.

VI. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Proteasome Activity Measurements.

Human purified proteasome complexes were purchased from Enzo LifeSciences or Boston Biochemicals (19S complex). BODIPY-casein (Invitrogen/Molecular Probes) was used as a model protein substrate, with increasing fluorescence of BODIPY labeled peptide products of degradation monitored for up to 8 hours at 37° C. The peptidase activity of the enzyme was measured as arbitrary intensity units of the released fluorescent group 7-amino-4-methylcoumarin (AMC) from peptide substrates, as described. The common substrates specific for the three kinds of active sites: succinyl-LeuLeuValTyr-7-amido-4-methylcoumarin (Suc-LLVY-MCA; for the ChT-L activity; Bachem), butoxycarbonyl-LeuArgArg-MCA (BocLRR-MCA; for T-L; Bachem) and carbobenzoxy-LeuLeuGlu-MCA (CbzLLE-MCA; for PGPH; Enzo Life Sciences International, Inc.) were used at 100 μM final concentrations, unless stated otherwise (Gaczynska and Osmulski, 2005). Proteasome substrates, rapamycin, its derivatives, and competing peptides were stocked in DMSO and diluted 100-fold in the reaction mixtures. The Rpt5 and PA200 C-terminal peptides were synthesized in the Departmental Peptide Synthesis Core using the standard SPPS chemistry. To activate the latent 20S proteasome, 0.005% (final concentration) of sodium dodecyl sulfate (SDS) was used. The reactions were carried out in 96 well plates, with 2.3 nM proteasome and other components as indicated dissolved in 50 mM Tris-HCl buffer (pH 8.0) and incubated at 37° C. for up to 1 hour. The fluorescence of products was monitored every 2 minutes with a Fluoroskan Ascent plate reader. Reaction rates were calculated from smoothed linear segment of kinetic curves using OriginPro 8.6 (OriginLabs, Northampton, Mass.). For the determination of an inhibition type, at least six distinct substrate concentrations and two inhibitor concentrations were used. The kinetic parameters of inhibition were analyzed in terms of the Michaelis-Menten formalism using the enzyme kinetic module of SigmaPlot v.12 (Systat Software, Inc, San Jose, Calif.) to perform the respective calculations.

Atomic Force Microscopy Imaging.

AFM imaging of the 20S proteasomes were performed as previously described, in tapping (oscillating) mode in liquid (Osmulski et al., 2009 and Gaczynska and Osmulski, 2011). In short, 3 μL of proteasome preparations diluted to nanomolar concentration were deposited on a freshly cleaved muscovite mica surface. After 2 min incubation allowing electrostatic attachment of the protein particles to mica the droplet was overlaid with 30 microL of 50 mM Tris-HCl buffer (pH 7.0) and mounted in the wet chamber of a MultiMode NanoScope Ma (Bruker Corp.). Oxide-sharpened silicon nitride tips on cantilevers with a nominal spring constant 0.32 N/m (Bruker Corp.) were used to image 1 μm$^2$ fields in the height mode, with a scan rate of 3.05 Hz. The excitation frequency was manually tuned to 9-10 kHz, with a drive voltage of 200-500 mV and a relatively high set point (1.6 V to 1.9 V) to assure tapping with low, non-destructive force. Trace and retrace images were collected with resolution of 512×512 pixels, which resulted in a digital (apparent) resolution of 2 nm in x and y directions. As the inventors established previously, such resolution was sufficient to detect distinct conformations of the α face, covered by six scan lines. Multiple fields were scanned for each sample to collect images of hundreds of particles. Selected fields were repeatedly scanned to monitor changes in topography of the same particles for prolonged time. Inhibitors and the SucLLVY-MCA substrate were diluted in 10 μL of the imaging buffer and directly injected into the chamber. Raw images are presented, with a standard plain-fit and flattening (NanoScope software v.5.12) used as the only processing tools. For display purposes the brightness and contrast of the images was adjusted with the Nanoscope software or with Adobe Photoshop (Adobe Systems Inc.), and outlier scan lines were occasionally manually removed (Nanoscope software). Top view ("standing", rounded) proteasomes were distinguished from the minor population of side-view ("lying", rectangular) particles as described, by comparison of their length—to width ratios (Osmulski et al., 2009). The dimensions of particles were approximated and a shape of the α face in top-view proteasomes was judged with the help of a section tool in the Nanoscope v.5.12 or SPIP v.6.02 software (Image Metrology).

Inhibition of Enzyme Activity.

$IC_{50}$ values (a drug concentration causing 50% inhibition of the indicated enzymatic activity) were calculated for ChT-L and PGPH peptidases. $K_d$ (dissociation constant) and $B_{max}$ (maximal activation effect achieved; in % above the control activity) values were calculated for the T-L peptidase. Mean±SD from n=2 or 3 experiments, or data from representative experiments set in duplicates or triplicates, are presented in the table. All three peptidase activities changed by no more than ±20%, without a concentration-dependent trend, upon treatment with up to 10 µM of rapamycin unrelated mTOR inhibitors PI-103 or NVP-BEZ235, in two independent experiments.

Example 2—Results

Rapamycin Noncompetitively Inhibits Proteolytic Activity of the 20S Proteasome.

Figure 3:
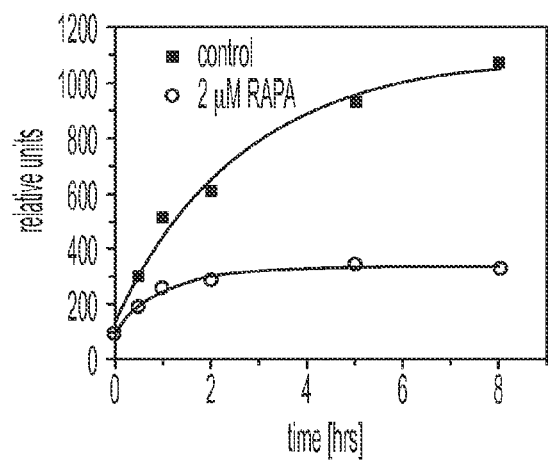
FIG. 3: Rapamycin inhibits degradation of casein by 20S proteasome. The fluorescently labeled BODIPY-casein was incubated with the human housekeeping core particle and the fluorescence of released BODIPY, free or attached to short peptide products of degradation, was monitored.

The core proteasome particle is capable of cleaving short peptides and poorly structured proteins, for example casein. The inventors tested first the influence of rapamycin on degradation of fluorescently labeled casein by the latent proteasome. An addition of 2 µM or 5 µM rapamycin slowed down the release of fluorescent products 2- to 3-fold (FIG. 3). Moreover, for the drug-treated proteasomes the release of new products almost ceased after 1 hour of incubation, whereas for the control enzyme accumulation of products continued for the 8 hour duration of the experiment. Degradation of a model protein engages all active sites of the proteasome. To gain insight into the effects of rapamycin on the performance of specific active sites, the inventors tested degradation of short model peptide substrates. Rapamycin inhibited post-acidic and post-hydrophobic peptidase activities of purified latent human proteasome in sub-micromolar to low micromolar concentrations, with $IC_{50}$ (concentration of an inhibitor inducing a 50% decrease of enzyme activity) of about 0.4 µM and 2 µM, respectively (Table 1). Titration curves for inhibition of ChT-L peptidase for housekeeping and immunoproteasome were undistinguishable (not shown), and the inventors used the housekeeping 20S in all subsequent experiments. Consistently with previously reported data, the detergent-activated CP was refractory to rapamycin up to concentration of about 5 µM, with only a weak inhibition of post-hydrophobic cleavages noted at higher drug concentrations. The rapamycin-20S interactions were fully reversible. In a representative experiment the incubation of CP with 2 µM rapamycin lowered the ChT-L peptidase activity to 52%. After a 10-fold dilution, the ChT-L peptidase was 99% active, as compared with the control treated with DMSO. The inhibition effect was reversible in the case of the PGPH peptidase as well. Namely, incubation of CP with 0.2 µM rapamycin lowered the PGPH peptidase activity to 48%, and the activity rebound to 96% of the control after a 10-fold dilution of the reaction mixture.

Figure 4A:
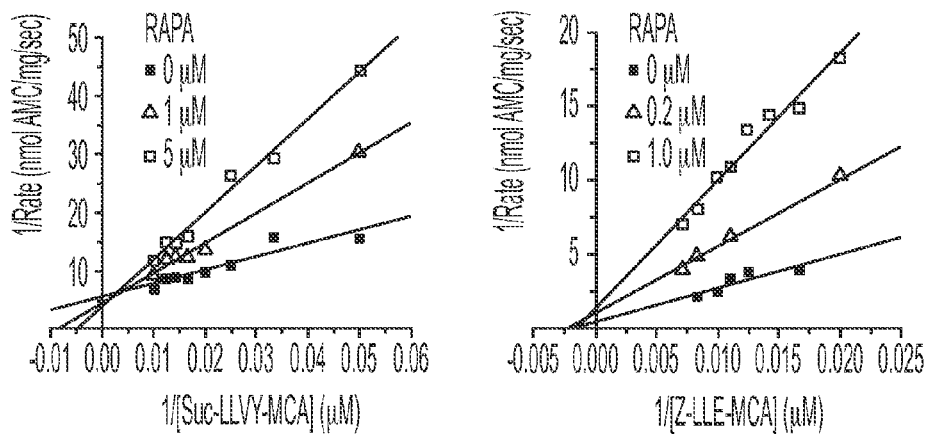
FIGS. 4A-B: Rapamycin inhibits the post-hydrophobic (ChT-L) peptidase of human core proteasomes. Rapamycin and its derivatives inhibit the post-hydrophobic (ChT-L) and post-acidic (PGPH) peptidases of human core proteasomes. The Lineweaver-Burk plots (top) and the dose response curves (bottom) of the control and rapamycin-treated proteasomes are shown in panels A (ChT-L) and B (PGPH). The data followed the mixed inhibition model for the post-hydrophobic cleavages (FIG. 4A top), with $R^2=0.958$. The corresponding Michaelis constant $K_M$ was 55.3 µM and $K_i=0.49$ µM. For the PGPH activity (FIG. 4B top) the corresponding values were $R^2=0.978$, $K_M=173$ µM, and $K_i=0.25$ µM. The single-domain derivative of rapamycin, FK-506, and the linear metabolite of rapamycin, seco-rapamycin, inhibits the ChT-L and PGPH peptidases (bottom panels). The corresponding $IC_{50}$ values are listed in Table 1. Means±SD (n=3-5) or results of representative experiments are presented.
Figure 4A:
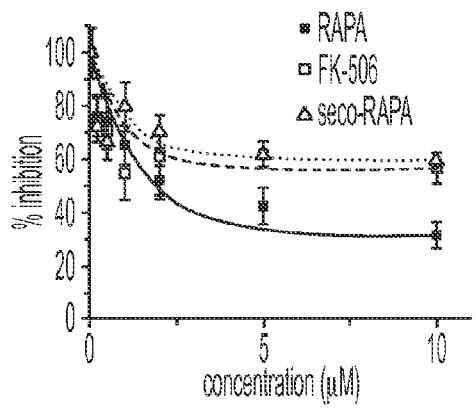
Figure 4B:
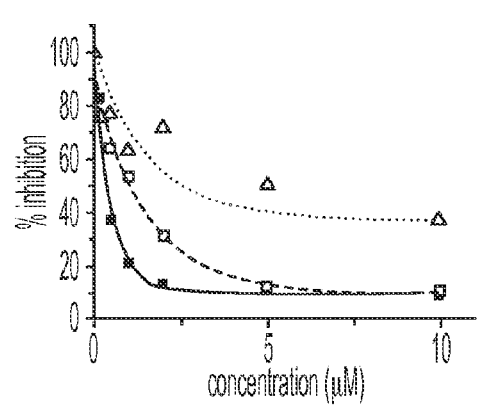

Analysis of peptide degradation in the presence of rapamycin indicated a pure noncompetitive inhibition for the post-acidic (PGPH) cleavages. On the other hand, the mixed type of inhibition was determined for the post-hydrophobic (ChT-L) proteasomal peptidase (FIGS. 4A-B). Similarly to certain other small noncompetitive ligands of the proteasome, the actions of rapamycin were not restricted to inhibition of the peptidases (Jankowska et al., 2010). The T-L peptidase was moderately activated by rapamycin. The activation of post-basic cleavages was of nonessential type, with nearly two-fold increase in activity and with the $K_d$ in the range of 0.1 µM.

Rapamycin Derivatives and Rapamycin Metabolite Affect the Activities of 20S Proteasome.

As a next step in this analysis, the inventors tested rapamycin-derived small ligands known as mTOR inhibitors. Modifications of rapamycin introduced on carbon-40 (temsirolimus, everolimus, and ridaforolimus), which is not directly involved in interactions with mTOR or FKBP12 (FIGS. 1A-D), did not abolish the inhibition of the proteasome. Just to opposite, temsirolimus was even a better inhibitor than rapamycin, with nearly 40% lower $IC_{50}$ for the ChT-L and 20% lower $IC_{50}$ for the PGPH peptidases (Table 1). It is worth to mention that temsirolimus (Torisel) and everolimus (Afinitor) are in clinical trials as anti-cancer drugs (Vignot et al., 2005). The rapalogs modified at the C-40 position retain the two pharmacophores characteristic for rapamycin, the binding and effector domains. In contrast, single domain rapamycin mimics inhibiting the mTOR pathway such as pimecrolimus and FK-506, preserve only the FKBP binding domain (FIGS. 1A-D). Nevertheless, both the compounds inhibited the two peptidase activities of the proteasome, albeit less efficiently than rapamycin or rapalogs (Table 1). The inhibition of post-acidic cleavages was the one least affected by the lack of effector domain, with the $IC_{50}$ increasing by only 40% in the case of pimecrolimus as compared with rapamycin. At low concentrations of the drugs the inhibitory effects of the single and two domain derivatives on the ChT-L activity were very similar. However, at higher concentrations of pimecrolimus and FK-506 the effects reached a plateau, whereas reduction of ChT-L activity with increasing concentrations of rapamycin and the rapalogs continued (Table 1). The two single-domain mimics activated the T-L peptidase even stronger than rapamycin, up to five-fold; however the maximal effect was reached at relatively high concentrations (Table 1).

In addition to two-domain analogs and single-domain mimics, the inventors tested seco-rapamycin, the open-ring first product of metabolism of rapamycin in human body (FIGS. 1A-D). Seco-rapamycin was reported not to affect the mTOR function (Cai et al., 2007). Surprisingly, the metabolite did affect the proteasome activities at the low micromolar concentrations, with the PGPH and T-L peptidases affected the most. The efficiency of inhibition or activation by seco-rapamycin was lower than by rapamycin, but still only 5 µM of the former was sufficient to inflict nearly a 50% inhibition of the post-acidic cleavages or almost a 2-fold activation of post-basic (T-L) cleavages. In contrast, all three proteasome peptidase activities were refractory to the treatment with up to 10 µM of PI-103 or NVP-BEZ235, the mTOR kinase inhibitors blocking its ATP-binding pocket that are structurally distinct from rapamycin (Table 1). Summarizing, all the tested rapamycin-related compounds exerted effects on the peptidase activities of human catalytic core proteasome.

Comparison of acquired $IC_{50}$ values revealed interesting trends in the inhibition potency among the rapamycin-related compounds. The post-hydrophobic (ChT-L) cleavages were much better inhibited by the two-domain compounds than by the single-domain and linear derivatives. When it came to post-acidic (PGPH) cleavages, both the two-domain and single-domain drugs were comparably good inhibitors, leaving the linear metabolite as a sole example of a weak inhibitor (Table 1). On the other hand, the significantly better maximal activation of the post-basic (T-L) cleavages was induced by the single-domain compounds. Surprisingly, the maximal T-L activation effect was observed at much lower concentrations of the two-domain drugs (Table 1). Summarizing, all the tested rapamycin-related compounds exerted easily measurable effects on the peptidase activities of human catalytic core proteasome. However, the efficiency of inhibition or activation was clearly related to the structural constrains of the rapamycin derivatives.

Rapamycin and its Derivatives Affect Conformation of the Proteasome α Face.

Figure 5A:
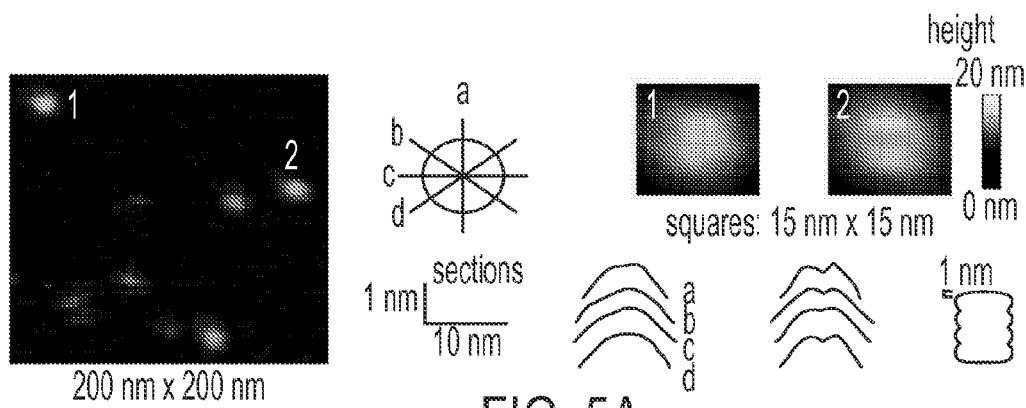
FIGS. 5A-F: Rapamycin and its derivatives affect conformational dynamics of the proteasome α face.
Figure 5B:
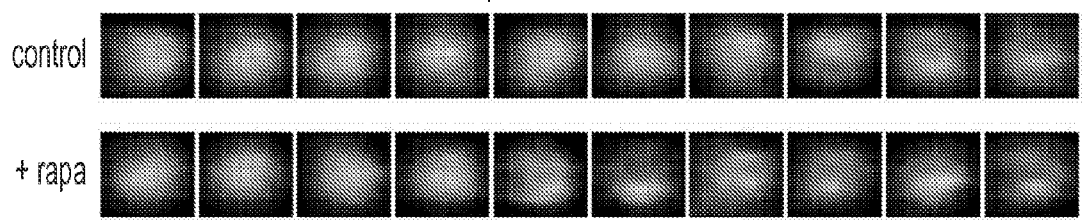
Figure 5C:
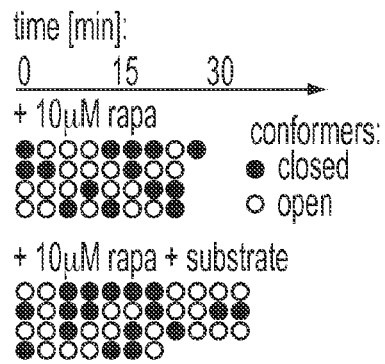
Figure 5E:
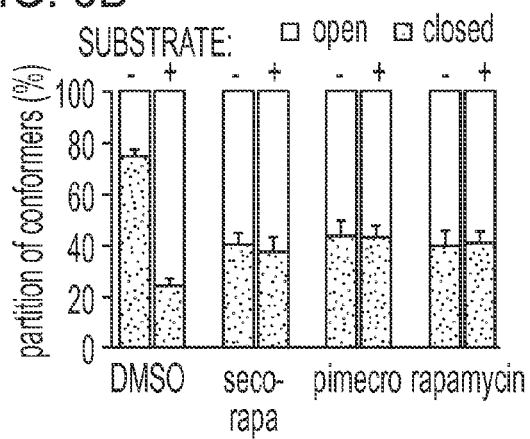
Figure 5D:
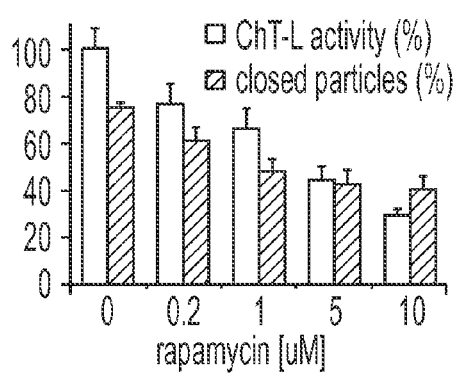

The noncompetitive nature of inhibition by rapamycin prompted us to search for the compound induced structural changes in the core proteasome. For this purpose, the inventors used the noninvasive tapping mode atomic force microscopy (AFM) in liquid, the imaging technique suitable for analysis of surface topography of macromolecules in their native state with a nanometer-scale practical resolution. The inventors established before that AFM imaging is a useful tool for studying structural dynamics of the 20S α face (Osmulski et al., 2009, Gaczynska et al., 2003; Gaczynska et al., 2011). They acquired and analyzed images of hundreds of single native, fully active 20S molecules. The majority of particles were in top-view ("standing") position conveniently allowing for imaging of their α faces. A closer analysis of the zoomed-in images of control human 20S proteasomes revealed the presence of two clearly distinguishable conformations: one with a smooth, cone-shaped α face, and another with a crater-shaped dip in the middle of α face, where the gate to the proteasome catalytic chamber is located. Following previous extensive studies, the inventors refer to the two forms as "closed-gate" and "open-gate" proteasomes, respectively (Osmulski et al., 2009). As described before, the inventors used the shape of sections carried out in four directions through the top portion of the surface topography of the α ring to distinguish between the two forms. In short, the particle was classified as closed if all four sections were cone-shaped. In contrast, the particle was classified as open if all sections presented a dip surrounded by a rim (FIG. 5A) (Osmulski, et al., 2009). The same particles imaged in consecutive scans were able to assume either closed or open conformations, however the cone-shaped particles were always more abundant than crater-shaped, and accounted for about three-quarters of the imaged molecules (FIG. 5B). Addition of rapamycin to the imaged particles remarkably changed the partition of forms. In the presence of rapamycin at concentrations as low as 0.2 μM, the closed forms accounted for 61% of proteasomes, a statistically significant (p<0.001) difference with the 75% closed CP registered for control proteasomes (FIGS. 5B-C). The abundance of closed molecules decreased with increasing concentration of rapamycin reaching 40% at 10 μM of the drug, and was paralleled by decreasing activities of the ChT-L peptidase (FIG. 5C). The rapamycin-treated particles retained their ability to switch between forms, similarly to the control particles treated with DMSO (FIG. 5D). The derivatives of rapamycin followed the parent drug in the ability to change the conformational equilibrium. The exposure to a high, saturating concentration (10 μM) of any of the three compounds: the linear metabolite (seco-rapamycin), the one-domain mimic (pimecrolimus) or the two-domain rapamycin resulted in a very similar final partition of conformers reaching about 60% open and 40% closed proteasomes (FIG. 5E). The conformational shift from 1:3 in control to the 3:2 partition of open to closed particles, albeit highly significant, was still less pronounced than a shift to the 3:1 partition the inventors observed before for eukaryotic proteasomes engaged in catalytic action (Osmulski et al., 2009). Therefore, they tested if the presence of rapamycin would affect the catalysis-related changes in the partition of conformers. The inventors added a model substrate for the post-hydrophobic peptidase to the 20S proteasomes already pretreated with rapamycin or its derivatives. Remarkably, the partition of conformers did not change significantly, in a sharp contrast with control proteasomes, which conformed to the expected 3:1 (open:closed) partition under the same conditions (FIG. 5E). The inventors also checked a response of CP topography to a treatment with PI-103, which as a nonallosteric mTOR kinase inhibitor does not significantly affect the proteasome activities in vitro. Proteasomes treated with PI-103 were undistinguishable from the DMSO-treated control, and followed the response of control particles to the treatment with the substrate (FIGS. 5A-F, caption and Table 1).

Figure 5F:
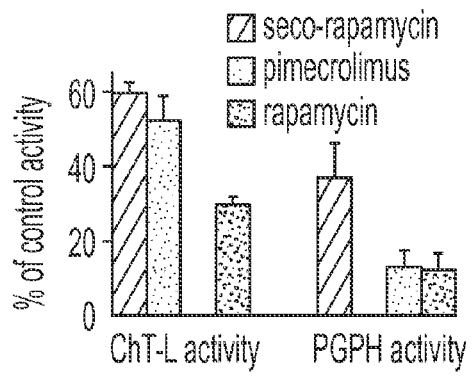

All the compounds at 10 μM concentration induced almost identical ultimate partition of the CP conformers what would suggest that CP achieved the maximum of structural response to the presence of the ligands detectable with AFM. In contrast, at this concentration each of the compounds also produced maximal but clearly a distinct level of peptidase inhibition (FIG. 5F).

Rapamycin and Related Compounds Interfere with Activation of the 20S by 19S Components.

Figure 6:
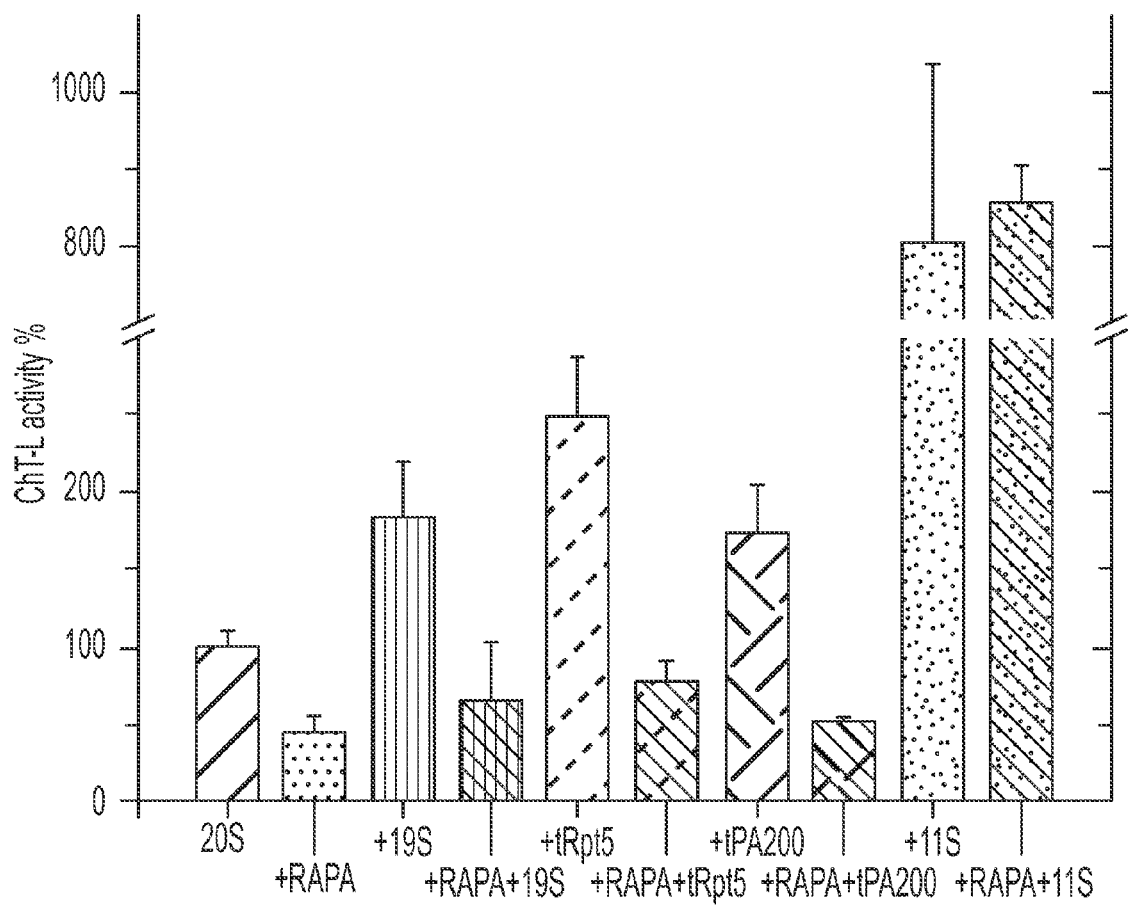
FIG. 6: Rapamycin interferes with activation of the 20S core by selected protein and peptide ligands of the α face. The relative ChT-L peptidase activity is presented as % of the control (20S with DMSO solvent). Specific activity of the control proteasome was in the range of 0.15 to 0.26 nanomoles of the AMC product released by mg of the 20S per second (0.20±0.03 nanomol of AMC/mg per sec; n=2 3). Values of mean±SD from n=3 to 7 independent experiments are presented. 5 µM rapamycin (RAPA) and 10 µM tRpt5 and tPA200 peptides were used, except the experiments with tPA200 where both compounds were used at 10 µM. 19S or 11S protein complexes were used in the 1:1 molar ratio with 20S. The differences between samples without and with rapamycin were statistically significant (p<0.01) except the samples liganded with 11S activator (green columns).

As demonstrated above, rapamycin interfered with dynamics of the proteasome gate located on the α face. This result prompted us to test if the drug would affect interactions of the 20S core with 19S regulatory particle, which binds to the α face. De novo assembly of 19S from subunits is a complex process assisted by chaperones. In vitro, and likely also in cells, the 26S can also be reconstructed from 20S and the already-assembled 19S particle in the presence of ATP (Smith et al., 2005). Enhancement of the peptidase activities of the core proteasome is an established test for efficiency of the in vitro reconstruction. Addition of RP to CP at the 1:1 molar ratio resulted in a two-fold increase of the ChT-L activity. In contrast, a pretreatment of 20S with 5 μM rapamycin before adding ATP and 19S totally abrogated the activation, leaving the proteasome almost 40% inhibited instead (FIG. 6). The activities of already assembled 26S proteasome were not significantly affected by rapamycin and related compounds at up to 10 μM concentrations (not shown).

Figures 2A, 2B, 2C, 2D:
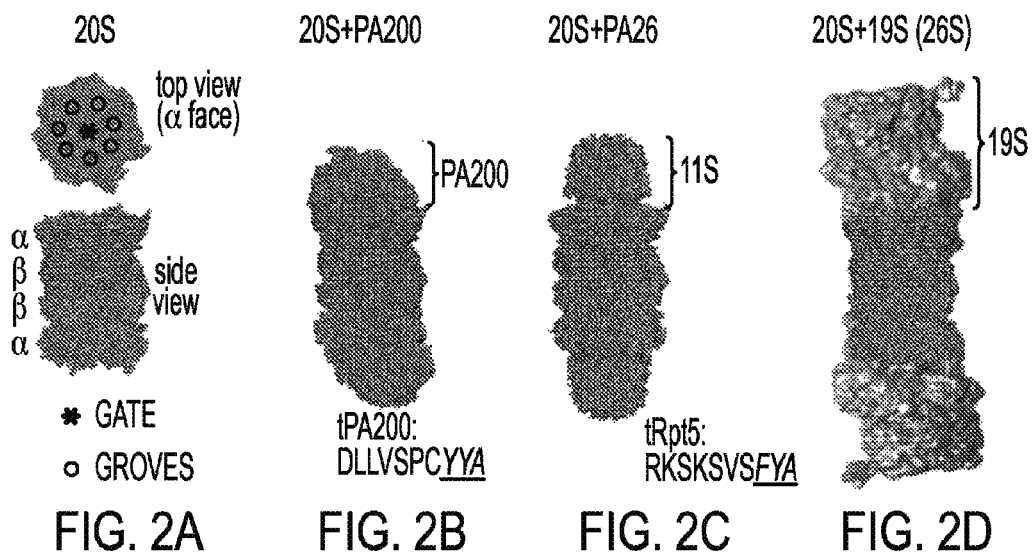
FIGS. 2A-D: The assemblies under the "proteasome" name.

Interestingly, the interference of rapamycin with the peptidase activation was not restricted to the interactions of CP with the entire 19S particle. It is established that the activation of CP by RP can be reproduced by C-terminal peptides derived from the selected ATPase subunits of the 19S. It has been determined previously that a 10 residue long peptide derived from the C-terminal segment of Rpt5 (tRpt5; FIG. 2D) exhibits the strongest activating effect. The inventors decided to test the influence of rapamycin on the activation imposed by tRpt5. Instead of the expected 2-fold activation of the core by the peptide, they observed an inhibition of CP even if a concentration of the tRpt5 peptide (10 μM) was two times higher than rapamycin (5 μM; FIG. 6). The tRpt5 was not the sole core-activating peptide derived from protein ligands attaching to the α face. The 10-residue C-terminal fragment of the activator protein PA200 (tPA200; FIG. 2B) shares with tRpt5 the capability to activate CP. Again rapamycin was abolishing the activation by the 10 μM tPA200 peptide. Addition of 10 μM rapamycin left the proteasome 50% inhibited instead of 2-fold activated (FIG. 6). The above trends were observed for the single-domain rapamycin mimic (FK-506) and the open metabolite (seco-rapamycin) as well. Their effects were the most pronounced in the presence of the tPA200: an addition of the 10 µM derivatives caused about 40% inhibition of the proteasome regardless the presence or absence of the 10 µM tPA200. FK-506 and seco-rapamycin interfered with activation of the core by the tRpt5 peptide, albeit not as efficiently as rapamycin. Upon treatment with either derivative (10 µM), the activation by the peptide (10 µM) was still well detectable, however it was about 30% lower than without the inhibitors. To the contrary, no detectable effects on activation of 20S with 19S were observed upon treatment with 5 µM PI-103.

Not all α face ligands were sensitive to the presence of rapamycin. An incubation of 20S with the heterohexameric PA29αβ/REGαβ (11S) at the 1:1 molar ratio increased the ChT-L peptidase activity 8-fold. The activation rates remained unaffected upon an addition of 5 µM of rapamycin before fortifying CP with the 11S complex (FIG. 6). Summarizing, rapamycin and its derivatives influenced functional effects of selected ligands of the α face, including the most physiologically relevant 19S regulatory particle.

Example 3—Discussion

Here, the inventors report that rapamycin, a canonical inhibitor of the mTOR kinase, affects in vitro performance of the 20S proteasome, the major intracellular protease in human cells. Rapamycin compromises degradation of the model protein and attenuates two out of three major peptidase activities of the proteasome. Analysis of the Michaelis-Menten enzyme kinetics revealed that rapamycin was a noncompetitive inhibitor of the PGPH activity and a mixed type inhibitor of ChT-L activity. The noncompetitive inhibition of the post-acidic cleavages implied that the inhibitor binds to the free and substrate bound enzyme with the identical affinity. In contrast, the mixed type inhibition of the post-hydrophobic peptidase suggested that rapamycin exhibited different affinity for the free proteasome and substrate-enzyme complex. These observations support a possibility that rapamycin affects each active site using distinct mechanisms. It influences the PGPH activity without apparent distinction between free and substrate bound forms of CP. In contrast, the inhibition of ChT-L activity is partially sourced to the competition with a substrate. Such a mechanism in turn indicates that the inhibitor preferentially binds to the free proteasome and cannot bind to a substrate-CP complex.

Since an addition of rapamycin leads to a substantial increase of the content of open gate particles that remain refractory to the substrate treatment, the inventors suspect the drug binds to the open form preventing it from closing. Intriguingly, rapamycin binding activates the trypsin like catalysis. This observation could be rationalized in terms of the closed gate playing the role of the "internal" inhibitor of T-L activity. One hypothesizes that for other activities rapamycin blocks completion of the catalytic cycle by depleting the content of closed form. The inventors previously established that the gate opening is associated with the catalytic cycle by allosteric signals propagated from the active sites to the α face and the gate (Osmulski et al., 2009). One can envision that similar signals are also sent into the opposite direction: from the α face to active centers. Obviously, the signals may also originate from other binding sites of rapamycin located beyond the α face. However, it is plausible that a short lived form of the active site associated with the open gate conformation is stabilized in its transition state by rapamycin what leads to the decreased productive substrate binding. Since the active centers so individually respond to the presence of rapamycin, it is likely that they are either differently sensitive to the ligand or substrate binding to particular active center induces a distinct CP affinity toward the ligand. The dramatic shift in the abundance of open conformation upon rapamycin binding would point to the former as the major underlying mechanism but does not exclude participation of the later. Based on these data, the inventors cannot decide if there is only one type of binding sites for rapamycin on each α face. The simplest regulation mechanism would involve a single binding site with a common allosteric path finally splitting to each active site. Therefore, even a single binding site may grant the noncompetitive and competitive inhibitory component in addition to the activating effect. Obviously, the gated, compartmentalized enzyme such as the proteasome provides many more none exclusive opportunities to bind a regulator of activity in the catalytic chamber, antechamber, central channel, the gating site, or the α face.

In this context, it is noticeable that all the compounds, regardless of their macrocyclic structure productively interact with the proteasome. It was rather surprising that the effector domain of rapamycin, missing in the single-domain derivatives was only beneficial but not essential for proteasome targeting. Even more remarkable, the presence of the closed macrocyclic structure was not essential either. Therefore, the macrocycle likely enforces the conformation supporting the most productive interactions with CP. Since effects of each compound on the individual activities were qualitatively similar, it is plausible that all of them utilize the same binding sites. Interestingly, the apparent binding affinity was only moderately sensitive to the substitution at the position C-40, what parallels the binding affinity to the original target since rapalogs with diverse C-40 substituents bind mTOR and FKBP12 similarly to rapamycin (Cai et al., 2007). Taken together, the data demonstrated possibility to design rapamycin-related compounds targeting the proteasome without directly influencing the mTOR pathway, similarly to seco-rapamycin.

These data strongly support the hypothesis that a significant part of the observed functional effects of the rapamycin related compounds on proteasome were allostery driven. The AFM detected shift in the abundance of open conformation details a topographic state of the gate area. This region is at least passively involved in a substrate passage into the catalytic chamber. Nevertheless, the binding of rapamycin to CP induced structural changes affecting both the gate and the performance of active centers. Since these elements are set at least 5 nm apart in CP, only allostery constitutes an acceptable mechanism explaining the long range effects. Furthermore, the competition between rapamycin and ligands that specifically bind to the α face suggests an important contribution from the allosteric mechanism. Finally, a non-allosteric inhibitor would physically hinder an access of substrates to the active sites. However, an obstruction of the path common for all the substrates, such as the gate or the central channel, would result in indiscriminate inhibition of not just two but all the proteasome peptidases. Importantly, all these α face ligands also induces opening of the gate similarly to the effect of rapamycin. On this basis, the inventors predict that the most influential rapamycin binding sites are positioned on the α face close to the binding sites of the 19S cap and PA200 activator. In summary, upon accepting rapamycin, the binding sites undergo structural changes that are propagated to the gate elements leading to its opening. This in turn induces the activation of an allosteric path that results in structural remodeling of active centers cumulating in substantial change in enzymatic efficiency of each catalytic site. The proposed chain of events does not preclude a possibility that the gate opening is just a side effect of ligand binding without a major contribution to the status of active centers. Interestingly, such a diversified influence of rapamycin on many aspects of the proteasome performance evokes other allosteric ligands, such as proline and arginine-rich (PR) peptides, TAT peptides, and certain proteins that bind to the α face (Gaczynska et al., 2003; Jankowska et al., 2010). They also induce changes in abundance of the α face conformers and affect the catalytic specificity of CP. Some of them also compete with the 19S RP and PA200 for the binding sites on the α face.

The AFM detected dynamics of the gate provided an additional line of evidence for the allosteric nature of rapamycin actions. The inventors already used AFM imaging of the proteasome α face to identify gate movements allosterically driven by structural changes in the active center (Osmulski, et al., 2009 and Gaczynska, et al., 2003). Moreover, they noticed conformational destabilization of the α face induced by ligand binding. The inventors demonstrated before that the gate of the latent, free core proteasome exists in a state of conformational equilibrium between the prevailing closed-gate state and the less populous open-gate state (Osmulski and Gaczynska, 2002). The inventors assume that the open-gate conformation enables substrates to enter the central channel and to reach the catalytic chamber, and thus the AFM-detected sporadic gate opening accounts for the detectable catalytic activity of the latent 20S proteasome. When a proteasome active site is working under the steady state conditions, the conformational equilibrium is shifted toward majority of the open-gate particles. The AFM showed that a treatment with rapamycin induced in a dose-dependent manner a shift of the conformational equilibrium toward moderately elevated incidence of the open-gate state. The content of the open gate CP was significantly higher than in the latent proteasome but substantially lower than in the proteasome engaged in catalytic action. Importantly, the abundance of the open conformers in the rapamycin treated proteasomes was refractory to an addition of the excess of a peptide substrate. The lower abundance of the open conformers likely compromises substrate gating and prevents the core proteasome from reaching its full catalytic potency. Rapamycin and its allies thus emerge as unique regulators affecting conformational dynamics of the target enzyme.

It seems that the perturbations of substrate gating amount for just a part of the inhibitory effects of the agents. Interestingly, the same partition of conformers in proteasomes induced by the high dose of distinct rapamycin derivatives resulted in very distinct levels of peptidase inhibition that clustered according to the number of the domains and preservation of the macrocycle. Moreover, the "maximal inhibitory effects" achieved with the saturating concentrations of the drugs were in perfect agreement with the $IC_{50}$ values. Overall, both the pharmacophore domains are required to reach the strong inhibition of the ChT-L peptidase. The presence of FKBP binding domain is sufficient for the effective inhibition of the PGPH peptidase. The inventors propose the following interpretation of the results, and hypothesize that interactions of the proteasome with all the tested compounds induce the maximal conformational shift resulting in the compromised gating of substrates.

These effects manifest in the weak-to-moderate inhibition of ChT-L and PGPH activities by seco-rapamycin. Pimecrolimus and rapamycin retain the full ability to trigger the conformational shift. However, the FKBP binding domain present in pimecrolimus and rapamycin enables interaction with a putative allosteric site responsible for strong inhibition of the PGPH activity. The effector domain as a second pharmacophore present in rapamycin might be engaged in additional interactions leading to a stronger attenuation of the ChT-L peptidase. Thus, the inhibition exerted by pimecrolimus and rapamycin would be a cumulative effect of the gate opening and inhibition via additional allosteric routes. The hypothesis would accommodate well the differences in inhibition type of the ChT-L and PGPH peptidases revealed by enzyme kinetic analysis. The pure noncompetitive inhibition of post-acidic (PGPH) cleavages may stem from interactions of two pharmacophores with the 20S proteasome: the putative pharmacophore present in all the studied rapamycin derivatives regardless of cyclization, and the FKBP binding domain of cyclic compounds. The mixed-type inhibition of post-hydrophobic (ChT-L) cleavages would then require yet additional pharmacophore, the effector domain, perhaps responsible for the competitive-like component in the inhibition mechanism. At this point it is impossible to decide if the compounds bind to one or more sites, and if binding to a single site affects one or more allosteric routes. Additional structural studies are necessary to verify the above speculations. Nevertheless, the data point at the importance of protein dynamics in biological catalysis, an emerging concept of great implications for the rational drug design and for protein engineering.

The putative binding sites of rapamycin and its derivatives remain unknown. Considering the described above functional effects it is plausible that the drug would bind on the outside of the proteasome core to the α face, which provides canonical binding sites used by multiple natural ligands. All the α face ligands tested here utilize groves between the a subunits as binding sites. The ligands can be classified into two groups. The 19S, Rpt5 peptide, and PA200 peptide belong to the first group characterized by the presence of an Hb-Y-X motif that serves as an anchor in selected, specific groves (Rabl et al., 2008). The 11S activator belongs to the second group: its subunits most likely occupy all seven groves simultaneously and do not have the Hb-Y-X motif (Whitby et al., 2000). Instead, each subunit relies on two binding sites: the C-terminus penetrates the grove, and the activation loop binds nearby to stabilize the docking (Whitby et al., 2000). Interestingly, the effects of pretreatment of the proteasome with rapamycin and related compounds were detectable only in the case of Hb-Y-X ligands. Therefore, one may speculate that rapamycin directly competes with canonical ligands for the same binding groves. They are already allosterically connected to the gate and, putatively, to the catalytic chamber. These connections can be utilized by rapamycin. Indeed, the molecular modeling data fully support effective docking of rapamycin to at least selected groves (Boehner, Gaczynska, Osmulski, unpublished observations). Additional experiments are under way to resolve the issue. Rapamycin binding apart from the groves or even apart from α face still cannot be excluded; however it would entail the presence of new potential binding sites and yet-unknown allosteric connections.

No competition of rapamycin was detected with the 11S particle. The affinity of PA28/REG subunits to the α face is likely much higher than affinity of rapamycin. One may envision that the 11S heptamer efficiently blocks access to all groves on the occupied α face, unlike the peptide ligands or, possibly, the wobbling—prone 19S cap. The results, however, suggest a more complex effect than a simple outcompeting the rapamycin by 11 S activator. Even when 11S was added to the 20S in a 1:1 molar ratio, the activity of a resulting assembly was not affected by rapamycin. The 20S has two α faces and the particle single-capped by 11S may still accept ligands on the opposite side. The lack of a rapamycin-induced effect can be explained by three non-excluding phenomena. First, binding the 11S on one side of 20S may allosterically lower the affinity of the other side to rapamycin. Second, single capping of 20S with 11S may abrogate the inhibitory effects of rapamycin already bound on the other side. These two options assume that practically all core particles are single capped with the 11S under these conditions. Third, adding rapamycin may result in a partition of 20S-11S (single capped) and 11S-20S-11S (double capped) complexes very distinct from the partition established in the absence of the drug. The shifts in partition resulting in specific alterations in activity may effectively obscure the effects of rapamycin. The experiments determining potential rapamycin-induced changes of 20S affinity to the protein regulators are under way.

The presented data demonstrate that rapamycin, its derivatives, and its metabolite are unexpected inhibitors of the catalytic core proteasome. They likely represent a novel molecular mechanism of action involving allosteric interactions. In vitro, they interfere with gating of substrates and with binding of the physiologically critical 19S assembly. One may hypothesize that the compounds affecting the 20S-19S interactions in vitro will also disturb the orchestrated assembly of 19S subunits on the α face in vivo. Two important questions should be asked about practical implications of the finding. First, does the effect have any significance in vivo, in humans or animals treated with rapamycin or rapalogs? Second, can the unique mechanism of action be of pharmacological use? The in vitro affinity of rapamycin and rapalogs to mTOR is much higher than to the proteasome, with $IC_{50}$ difference in a range of at least two orders of magnitude. One could expect that in vivo consequences of mTOR inhibition will be evident with much lower dose of the drug than any direct effects on the proteasome. Still, the inhibition of the proteasome core and/or a decrease in the content of properly assembled 26S proteasome may be detectable after a local accumulation of the drug. Even more intriguing is the possibility that seco-rapamycin as a metabolite of rapamycin exerts significant effects on the proteasome while not affecting mTOR. Indeed, optimization of seco-rapamycin structure for specific proteasome targeting should be a prime goal. One may speculate that such compound (and, at present, seco-rapamycin) will have distinct intracellular effects than bortezomib and other common competitive inhibitors of proteasome. The inventors predict that unlike with competitive inhibitors, which block free or capped 20S proteasomes alike, free 20S proteasomes will be affected first by the allosteric drug inspired by rapamycin. The free core proteasomes are believed to exist in a cell where they are involved in ubiquitin-independent degradation of proteins with intrinsically disordered domains, such as certain transcription factors, or proteins partially unfolded by stressors. The physiological significance of the free 20S is still debated; however the inhibition of this form would be expected to affect at least specific degradation of the selected disordered or unfolded substrates (Liu et al., 2003; Pickering et al., 2010). The cellular effects of rapamycin-like inhibitor on ubiquitin-dependent degradation will likely unfold slowly, as the cell will attempt to replace the existing 26S complexes with the new particles, and de novo assembly of 26S will be compromised by the presence of the drug. It is tempting to speculate that such gradual process will help to avoid drug resistance in cancer cells. Summarizing, the allosteric inhibitors affecting the proteasomal α face may constitute important tools to control proteasome catalytic activity and useful probes to test its molecular mechanism. These properties may put rapamycin-based compounds in the forefront of search for pharmacologically useful allosteric regulators of the ubiquitin proteasome pathway.

TABLE 1

Rapamycin and related compounds affect peptidase activities of the 20S proteasome in sub-micromolar to low-micromolar concentrations.

| COMPOUND | $IC_{50}$ [μM]: ChT-L | $IC_{50}$ [μM]:: PGPH | $K_d$ [μM]: T-L | $B_{max}$ [%]: T-L |
|---|---|---|---|---|
| rapamycin | 1.9 ± 0.2 | 0.41 ± 0.03 | 0.14 | 83 |
| temsirolimus | 2.1 ± 0.2 | 0.36 ± 0.03 | 0.19 | 81 |
| everolimus | 2.5 ± 0.7 | 0.48 ± 0.11 | 0.07 | 93 |
| ridaforolimus | 2.9 ± 0.5 | 0.43 ± 0.11 | 0.11 | 114 |
| pimecrolimus | >20 | 0.57 ± 0.12 | 1.82 | 483 |
| FK-506 | >20 | 0.93 ± 0.04 | 1.14 | 257 |
| seco-rapamycin | >20 | 6.45 ± 0.78 | 5.33 | 77 |

[a] The ChT-L activity did not reach 50% inhibition at concentrations up to 20 μM upon treatment with single-domain or open-ring rapamycin derivatives. However, a reproducible inhibition of up to 40% was obtained with the drugs at the concentration as low as 1 μM. At this concentration the inhibitory effects of all the rapamycin related compounds were similar.
[b] The two-fold activation of T-L activity with was observed at as low concentrations as 0.5 μM-1 μM of the single-domain compounds.

Example 4—Materials and Methods

Cells and Culture Conditions.

The following human cancer cell lines (American Type Culture Collection; ATCC) were cultured according to ATCC specifications: HeLa.S3 cervical adenocarcinoma, MCF7 breast adenocarcinoma, MDA-MB-231 breast adenocarcinoma (representing triple negative breast cancer), and RPMI 8226 myeloma. The cells were grown in 24 or 12-well cell culture plates. When the cells reached about 60% confluency (surface-growing HeLa.S3,MCF7 and MDA-MB-231) or a density of about 7×10$^5$ (suspension-growing RPMI 8226), the inhibitors dissolved in DMSO or the solvent (DMSO) diluted in respective culture medium were added and the cells were further cultured for additional 48 hours. The final concentrations of bortezomib and seco-rapamycin are indicated below. The final concentration of the solvent was 1% (vol/vol). The number of live and dead cells after the treatment was approximated with calcein AM and ethidium homodimer (LiveDead test, Invitrogen) according to manufacturer's protocol, or by a Trypan Blue exclusion assay. In short, the cells after the treatment were washed three times with PBS and overlaid (surface-growing) or mixed (suspension-growing) with 4 microM calcein AM and 2 microM ethidium homodimer in PBS. Fluorescence of calcein and DNA-bound ethidium homodimer was measured with Fluoroskan Ascent plate reader, at 485 nm (excitation)/538 nm (emission) and 530 nm/619 nm, respectively. The cell counts were approximated using standard curves of live and digitonin-killed cells prepared for each strain. Alternatively, after cell treatment the medium was removed, the surface growing cells were overlaid with Trypan Blue solution, and the colorless (live) and blue-colored (dead) cells were counted under the inverted microscope.

Assay.

The in vitro assay for testing the ChT-L peptidase activity of the purified human 20S proteasome was performed as described above. Results of representative experiments are shown.

Example 5—Results

Rapamycin and its close derivatives are cytotoxic, a feature utilized for treatment of selected cancers with rapalogs temsirolimus (Torisel) and everolimus (Afinitor). However, the actions of these drugs have been ascribed to inhibition of the mTOR and disrupting of the mTOR pathway. The first stable metabolite of rapamycin, the open ring seco-rapamycin (FIG. 1C) was reported not to affect the mTOR kinase activity. Since seco-rapamycin or the open-ring derivatives of rapalogs can accumulate in patients treated with the respective closed-ring compounds, the inventors tested the effects of seco-rapamycin on cultured cells.

Figure 7:
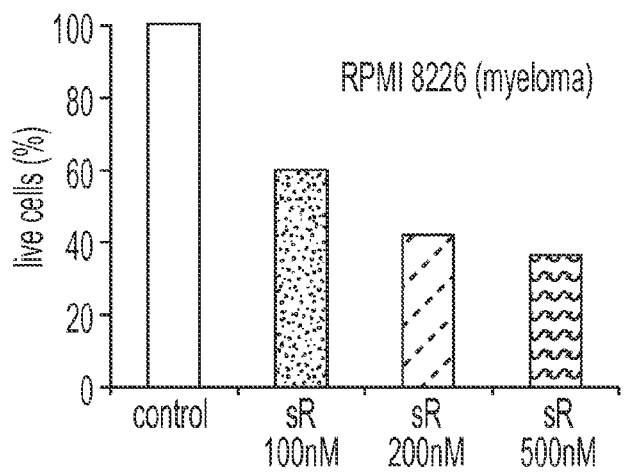
FIG. 7: Seco-rapamycin is toxic to RPMI 8226 myeloma cultured cells. Results of representative experiment of 48 hrs of treatment with seco-rapamycin (sR) are shown. Under the same conditions, treatment with 5 nM bortezomib resulted in 10% of remaining live cells and 18% of dead cells. 100% designated the number of live cells in the DMSO-treated control. The number of dead cells was consistently on the level of 12% to 18%, when the total cell count (live+dead) was calculated as 100%.
Figure 8A:
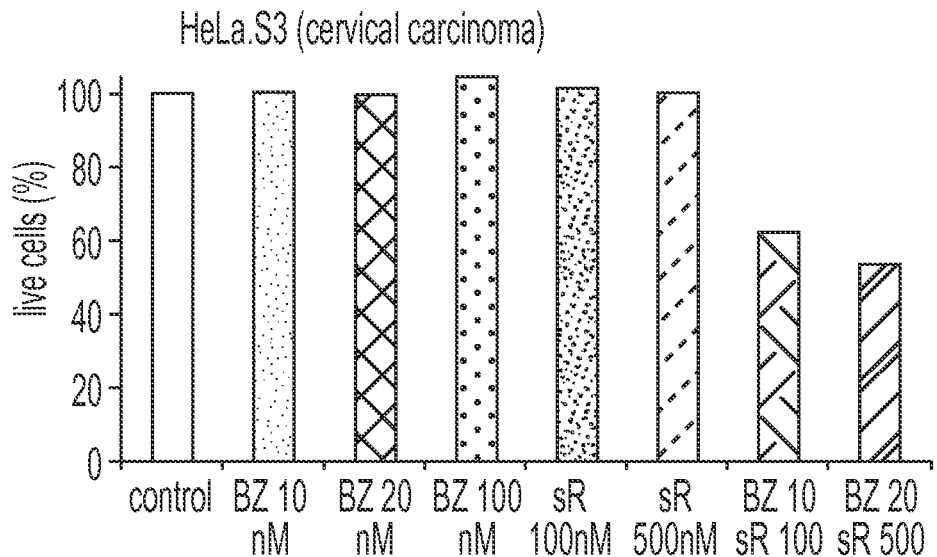
FIGS. 8A-D: Seco-rapamycin sensitized cultured cells derived from solid cancers to anti-cancer drug bortezomib.

Interestingly, the canonical multiple myeloma cell line RPMI 8226 was sensitive to the treatment with high nanomolar concentrations of seco-rapamycin. As low as 100 nM seco-rapamycin resulted in a 50% drop in the live cell count, and 200 nM of the metabolite left only one-third of the control cells alive (FIG. 7). The cell lines derived from solid cancers such as HeLa.S3 cervical carcinoma or MCF7 and MDA-MB-231 breast carcinomas were poorly responsive or refractory to the treatment with the canonical active center blocking inhibitor, bortezomib. Treatment of HeLa.S3 cells with up to 100 nM of bortezomib did not induce significant changes in cell proliferation (FIG. 8A) or in the number of dead cells, which accounted for up to 16% of the total cell count in DMSO-treated and bortezomib-treated samples. Similarly, treatment with up to 500 nM of seco-rapamycin did not reveal cytotoxicity. However, a combination treatment with high nanomolar concentrations of seco-rapamycin and bortezomib delivered an about 50% drop in the live cell count (FIG. 8A).

Figure 8B:
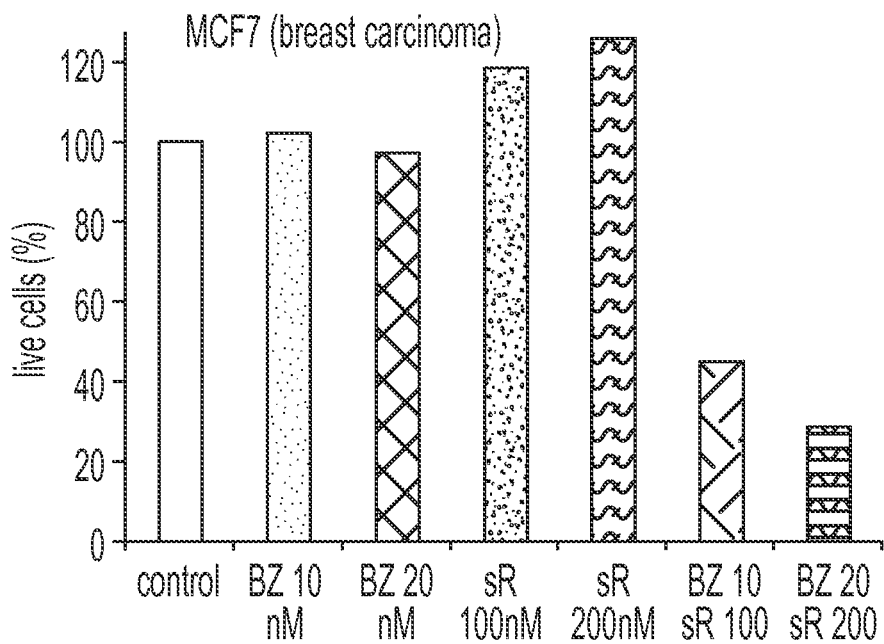
Figure 8C:
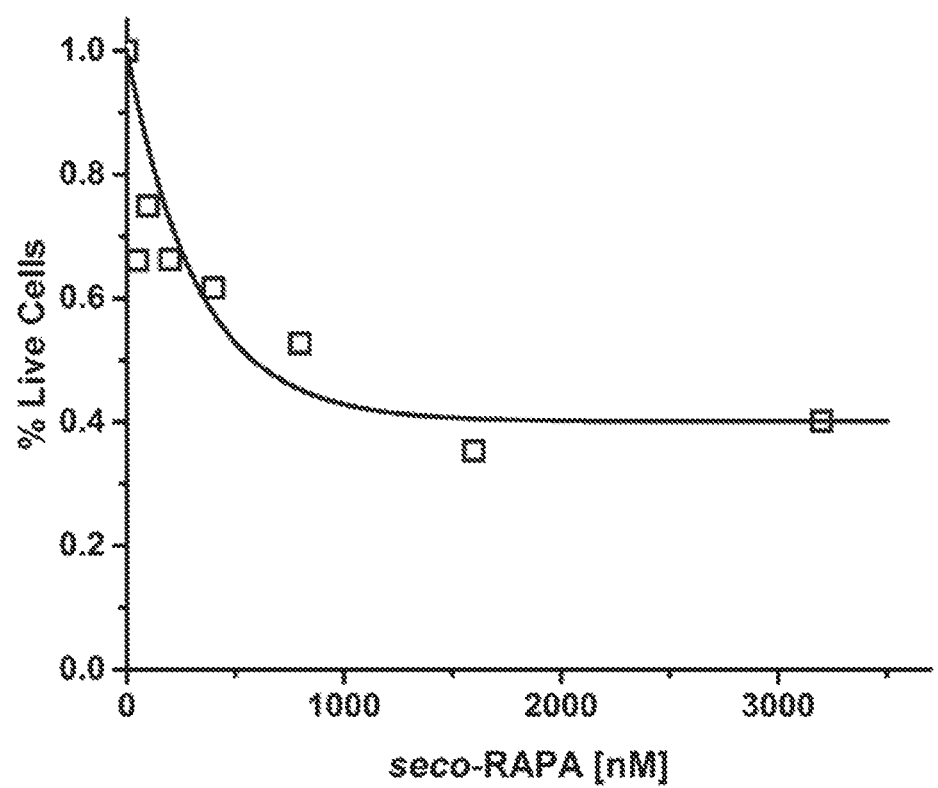
Figure 8D:
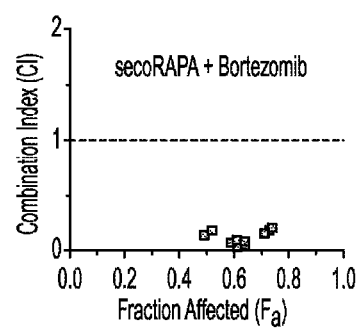

The benefits of combination treatment were evident in the case of MCF7 breast cancer cell line as well (FIG. 8B). For example, the treatment with 100 nM seco-rapamycin and 10 nM bortezomib resulted in more than 50% drop in the live cell count, as compared with the DMSO-treated control or cell treated with the respective inhibitors used separately. Only about 30% of cells were alive after treatment with 200 nM seco-rapamycin combined with 20 nM bortezomib (FIG. 8B). It is worth to mention that 100 nM bortezomib was needed to lower the live cell count to about 53% of the control. Apparently, addition of 100 nM seco-rapamycin allowed achieving a similar cytotoxic effect with 10-fold lower concentration of bortezomib. Remarkably, the combination treatment with bortezomib and seco-rapamycin was especially effective with MDA-MB-231 breast cancer cells. FIG. 8 shows that seco-rapamycin alone (FIG. 8C), or in synergy with bortezomib (FIG. 8D), attenuates growth of MDA-MB-231 breast cancer cultured cell line representing basal B triple-negative breast cancers, which are particularly hard to treat.

Figure 9:
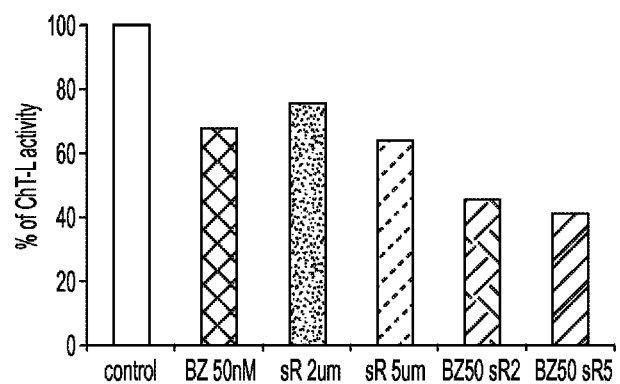
FIG. 9: Purified human 20S proteasome was inhibited by the combination of seco-rapamycin (sR) and bortezomib (BZ) stronger than by the compounds used alone. The leading ChT-L peptidase activity was tested with the model peptide substrate, suc-LLVY-MCA. Activity of DMSO-treated control proteasomes is shown as 100%. Under the same conditions, a combination of 50 nM bortezomib and 5 µM pimecrolimus resulted in 49% of remaining activity, as compared with 68% and 82% of remaining activity after treatment with BZ or pimecrolimus alone, respectively.

The beneficial effects of combination treatment with bortezomib and seco-rapamycin were detectable in the in vitro assay with the purified human 20S proteasome. The activity of chymotrypsin-like proteasomal peptidase, which is the major target of bortezomib, was tested. Incubation with 50 nM bortezomib or low-micromolar concentrations of seco-rapamycin resulted in less than 40% of the proteasome inhibition (FIG. 9). However, combining the two compounds increased the inhibition effect to more than 60% (FIG. 9). The inventors also used the in vitro activity assay to test the inhibition of the purified proteasome by combination of bortezomib with the parent drug, rapamycin (FIG. 1A), and the single-domain rapamycin derivative, pimecrolimus (FIG. 1B). The mTOR protein is the primary in vivo target of rapamycin and pimecrolimus, but not seco-rapamycin. The synergistic effect with bortezomib was apparent for all derivatives tested (FIG. 9).

FIGS. 10A-E show in vitro studies demonstrating the synergy of seco-rapamycin and rapamycin with competitive inhibitors of the proteasome. The inhibitors represent three classes of drugs used in clinics: boronates (bortezomib), epoxyketones (carfilzomib) and lactones (lactacystin). FIGS. 10A and 10C show in vitro synergistic effects of rapamycin+bortezomib and seco-rapamycin+bortezomib, respectively, on the inhibition of ChT-L activity of human purified CP. FIG. 10E shows in vitro synergistic effects of seco-rapamycin+carfilzomib (Kyprolis™) on the inhibition of ChT-L activity of human purified CP. Carfilzomib has been recently FDA approved to treat blood cancers. FIGS. 10B and 10D show in vitro synergistics effect of rapamycin+lactacystin and seco-rapamycin+lactacystin, respectively, on the inhibition of ChT-L activity of human purified CP. In water-based solutions, lactacystin breaks to clasto-lactacystin-beta lactone, which is a competitive inhibitor of the proteasome. A derivative of lactacystin, marizomib, is in clinical trials for blood cancers.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. References

The following references, to the extent that they provide exemplary procedural or other details supplementary to those set forth herein, are specifically incorporated herein by reference:

Adams, *Nat. Rev. Cancer* 4, 349-360, 2004.
Babbitt et al., *Cell* 121, 553-65, 2005.
Bajorek et al., *Current Biology* 13, 1140-4, 2003.
Banaszynski et al., *J. Am. Chem. Soc.* 127, 4715, 2005.
Baselga et al., *J. Clin. Oncology* 27, 2630-2633, 2009.
Cai et al., *Drug Metabol. Dispos.* 35, 1554-1563, 2007.
Ciechanover, *Biochim. Biophys. Acta Proteins Proteomics* 1824, 3-13, 2012.
Coleman et al., *Cell Prolif.* 39, 599-609, 2006.
Crawford and Irvine, *Blood Reviews, in press,* 2013.
Cresta et al., *European Journal of Cancer* 44, 1829-1834, 2008.
Da Fonseca et al., *Molecular Cell* 46, 54-66, 2012.
De Wilt et al., *Biochem. Pharmacol.* 83, 207-217, 2012.
Dowling et al., *BioDrugs* 23, 77-91, 2009.
Farag et al., *Leukemia Research* 43, 1475-1482, 2009.

Fenical et al., *Bioorg. Med. Chem.* 17, 2175-2180, 2009.
Gaczynska et al., *Biochemistry* 42, 8663-8670, 2003.
Gaczynska and Osmulski, *Methods in Molecular Biology* 301, 3-22, 2005.
Gaczynska and Osmulski, *Methods in molecular biology (Clifton, N.J.)* 736, 117-132, 2011.
Gao et al., *J. Clin. Invest.* 106, 439-448, 2000.
Goodey and Benkovic, *Nature Chemical Biology* 4, 474-482, 2008.
Groll et al., *Nature.* 386, 463-71, 1997.
Groll et al., *Nature* 452, 755-759, 2008.
Harrison et al., *Nature* 460, 392-395, 2009.
Jankowska et al., *Biopolymers* 93, 481-495, 2010.
Jankowska et al., *Curr. Pharm. Design* 19, 1010-1028, 2013.
Jin et al., *Bio. Pharm. Bulletin* 32, 988-992, 2009.
Kleijnen et al., *Nature Structural and Molecular Biology* 14, 1180-1188, 2007.
Konings et al., *Current Cancer Drug Targets* 9, 439-445, 2009.
Lander, et al., *Nature* 482, 186-191, 2012
Li et al., *Nat. Med.* 6, 49-55, 2000.
Li et al., *J. Natl. Cancer Inst.* 102, 1069-1082, 2010.
Liang et al., *Acta Crystallogr. Sect. D Biol. Cryst.* 55, 736, 1999.
Liu et al., *Science.* 299, 408-11, 2003.
Orlowski and Kuhn, *Clinical Cancer Research* 14, 1649-1657, 2008.
Ortega et al., *Journal of Molecular Biology* 346, 1221-7, 2005.
Osmulski and Gaczynska, *Biochemistry* 41, 7047-7053, 2002.
Osmulski et al., *Structure* 17, 1137-1147, 2009.
Pickering et al., *Biochem. J* 432, 585-594, 2010.
Rabl et al., *Mol. Cell* 30, 360-368, 2008.
Rechsteiner and Hill, *Trends in Cell Biology* 15, 27-33, 2005.
Roelofs et al., *Nature* 459, 861-865, 2009.
Smith et al., *Mol. Cell* 20, 687-698, 2005.
Sprangers and Kay, 2007.
Tan et al., *Current Medicinal Chemistry* 13, 155-165, 2006.
Unno et al., *Journal of Biochemistry.* 131, 171-3, 2002.
Vaziri et al., *Anticancer Research* 29, 2961, 2007
Vignot, *Annals of Oncology* 16, 525-537, 2005.
Wang et al., *Eur. J Immunol.* 27, 2781-2786, 1997.
Whitby et al., *Nature* 408, 115-20, 2000.

The invention claimed is:

1. A method of sensitizing a bortezomib-resistant cervical cancer cell to bortezomib in a subject comprising contacting said bortezomib-resistant cervical cancer cell with seco-rapamycin in an amount sufficient to inhibit said cancer cell.

2. The method of claim 1, wherein the subject is a human.

3. The method of claim 1, wherein further comprising contacting said cancer cell with a proteasome inhibitor binding to one or all types of proteasome active sites.

4. The method of claim 3, wherein the proteasome inhibitor is selected from the group consisting of boronates, epoxyketones, lactones, aldehydes, vinyl sulfones and syrbactins.

5. The method of claim 1, wherein contacting occurs multiple times.

6. The method of claim 5, wherein between multiple contacting events said cell is not exposed to seco-rapamycin.

7. The method of claim 1, wherein inhibiting comprises slowing growth of said cancer cell, inducing growth arrest of said cancer cell, or inducing death of said cancer cell.

8. The method of claim 3, further comprising administering to said subject rapamycin or a rapalog.

9. A method of treating a subject having breast cancer or a myeloma comprising administering to said subject with seco-rapamycin in an amount sufficient to treat said breast cancer or myeloma.

10. The method of claim 9, wherein the cancer cell is bortezomib-resistant cancer.

11. The method of claim 9, further comprising contacting said cancer cell with a proteasome inhibitor binding to one or all types of proteasome active sites.

12. The method of claim 11, wherein the proteasome inhibitor is selected from the group consisting of boronates, epoxyketones, lactones, aldehydes, vinyl sulfones and syrbactins.

13. The method of claim 12, wherein the cancer is bortezomib-resistant cancer.

14. The method of claim 9, wherein administering occurs multiple times.

15. The method of claim 14, wherein between multiple administrations said subject is not exposed to seco-rapamycin.

16. The method of claim 9, wherein the cancer is not a bortezomib-resistant cancer.

17. The method of claim 11, wherein the proteasome inhibitor is bortezomib.

18. The method of claim 9, wherein treating comprises slowing growth of said cancer, inducing growth arrest of said cancer, inducing programmed death in cells of said cancer, rendering an unresectable cancer resectable, inducing tumor tissue necrosis, extending said subject's lifespan, or improving said subject's quality of life.

19. The method of claim 10, wherein said subject has previously received bortezomib.

20. The method of claim 10, wherein said subject has not previously received bortezomib.

21. The method of claim 9, wherein said cancer is recurrent and/or metastatic.

22. The method of claim 17, wherein bortezomib is administered prior to seco-rapamycin.

23. The method of claim 17, wherein bortezomib is administered after seco-rapamycin.

24. The method of claim 17, wherein bortezomib is administered at the same time a seco-rapamycin.

25. The method of claim 17, wherein bortezomib is administered alternating with seco-rapamycin.

26. The method of claim 9, wherein administering comprises intravenous, intra-arterial, intra-tumoral, subcutaneous, topical or intraperitoneal administration.

27. The method of claim 9, wherein administering comprises local, regional, systemic, or continual administration.

28. The method of claim 9, wherein said subject is a human.

29. The method of claim 11, further comprising administering to said subject rapamycin or a rapalog.

30. The method of claim 9, wherein the subject has breast cancer.

31. The method of claim 9, wherein the subject has myeloma.

* * * * *